US011578016B1

(12) United States Patent
Solami et al.

(10) Patent No.: US 11,578,016 B1
(45) Date of Patent: Feb. 14, 2023

(54) OLEFIN PRODUCTION VIA DRY REFORMING AND OLEFIN SYNTHESIS IN A VESSEL

(71) Applicant: Saudi Arabian Oil Company, Dhahran (SA)

(72) Inventors: Bandar Solami, Dhahran (SA); Aqil Jamal, Dhahran (SA); Kunho Lee, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/400,833

(22) Filed: Aug. 12, 2021

(51) Int. Cl.
*C07C 1/04* (2006.01)
*B01J 8/02* (2006.01)
*C25B 1/04* (2021.01)
*C25B 15/08* (2006.01)
*C01B 3/40* (2006.01)

(52) U.S. Cl.
CPC ............ *C07C 1/0485* (2013.01); *B01J 8/025* (2013.01); *B01J 8/0278* (2013.01); *B01J 8/0285* (2013.01); *C01B 3/40* (2013.01); *C07C 1/041* (2013.01); *C07C 1/042* (2013.01); *C25B 1/04* (2013.01); *C25B 15/081* (2021.01); *B01J 2208/00026* (2013.01); *B01J 2208/00548* (2013.01); *C01B 2203/0238* (2013.01); *C01B 2203/062* (2013.01); *C01B 2203/1241* (2013.01); *C01B 2203/169* (2013.01); *C01B 2203/1614* (2013.01)

(58) Field of Classification Search
CPC .............. C01B 3/40; C01B 2203/0238; C01B 2203/062; C01B 2203/1241; C01B 2203/1614; C01B 2203/169; C07C 1/0485; C07C 1/042; C07C 1/041
See application file for complete search history.

(56) References Cited

U.S. PATENT DOCUMENTS

| 978,576 A | 12/1910 | Goodell |
| 2,694,678 A | 1/1951 | George et al. |
| 2,614,066 A | 10/1952 | Cornell |
| 2,753,301 A | 7/1956 | Bersworth et al. |

(Continued)

FOREIGN PATENT DOCUMENTS

| AU | 2003286894 | 6/2004 |
| AU | 2005286952 | 3/2006 |

(Continued)

OTHER PUBLICATIONS

Chen et al., Techno-economic evaluation of CO2-rich natural gas dry reforming for linear alpha olefins production (Energy Conversion and Management 205 (2020) 112348).*

(Continued)

*Primary Examiner* — Jafar F Parsa

(74) *Attorney, Agent, or Firm* — Fish & Richardson P.C.

(57) ABSTRACT

A system and method for producing olefin via dry reforming and olefin synthesis in the same vessel, including providing feed including methane and carbon dioxide to the vessel, converting methane and carbon dioxide in the vessel into syngas (that includes hydrogen and carbon monoxide) via dry reforming in the vessel, and cooling the syngas via a heat exchanger in the vessel. The method includes synthesizing olefin from the syngas in the vessel, wherein the olefin includes ethylene, propylene, or butene, or any combinations thereof.

12 Claims, 4 Drawing Sheets

(56) References Cited

U.S. PATENT DOCUMENTS

| | | |
|---|---|---|
| 2,910,426 A | 10/1959 | Gluesenkamp |
| 3,278,268 A | 10/1966 | Pfefferle, Jr. |
| 3,409,540 A | 11/1968 | Gould et al. |
| 3,533,938 A | 10/1970 | Arnold |
| 3,702,292 A | 11/1972 | Burich |
| 3,726,789 A | 4/1973 | Kovach |
| 3,755,143 A | 8/1973 | Hosoi et al. |
| 3,856,659 A | 12/1974 | Owen |
| 3,979,757 A | 9/1976 | Kilby et al. |
| 4,090,949 A | 5/1978 | Owen et al. |
| 4,134,824 A | 1/1979 | Kamm et al. |
| 4,264,435 A | 4/1981 | Read, Jr. et al. |
| 4,297,203 A | 10/1981 | Ford et al. |
| 4,426,276 A | 1/1984 | Dean et al. |
| 4,466,946 A | 8/1984 | Goddin, Jr. et al. |
| 4,527,003 A | 7/1985 | Okamoto et al. |
| 4,587,011 A | 5/1986 | Okamoto et al. |
| 4,589,896 A | 5/1986 | Chen et al. |
| 4,655,904 A | 4/1987 | Okamoto et al. |
| 4,717,407 A | 1/1988 | Choe et al. |
| 4,725,349 A | 2/1988 | Okamoto et al. |
| 4,786,400 A | 11/1988 | Farnsworth |
| 4,830,728 A | 5/1989 | Herbst et al. |
| 4,981,676 A | 1/1991 | Minet et al. |
| 4,992,160 A | 2/1991 | Long et al. |
| 5,091,351 A | 2/1992 | Murakawa et al. |
| 5,108,581 A | 4/1992 | Aldridge |
| 5,140,049 A | 8/1992 | Fiato et al. |
| 5,229,102 A | 7/1993 | Minet et al. |
| 5,366,712 A | 11/1994 | Violante |
| 5,401,300 A | 3/1995 | Lokhandwala et al. |
| 5,407,466 A | 4/1995 | Lokhandwala et al. |
| 5,407,467 A | 4/1995 | Lokhandwala et al. |
| 5,746,985 A | 5/1998 | Takahashi |
| 5,837,032 A | 11/1998 | Moll et al. |
| 5,904,837 A | 5/1999 | Fujiyama |
| 5,906,728 A | 5/1999 | Iaccino et al. |
| 5,951,850 A | 9/1999 | Ino et al. |
| 5,997,594 A | 12/1999 | Edlund et al. |
| 6,033,555 A | 3/2000 | Chen et al. |
| 6,119,606 A | 9/2000 | Clark |
| 6,153,163 A | 11/2000 | Prasad |
| 6,179,900 B1 | 1/2001 | Behling et al. |
| 6,180,081 B1 | 1/2001 | Poschmann et al. |
| 6,190,533 B1 | 2/2001 | Bradow et al. |
| 6,210,562 B1 | 3/2001 | Xie et al. |
| 6,214,485 B1 | 4/2001 | Barnett et al. |
| 6,274,032 B2 | 8/2001 | Hood et al. |
| 6,293,979 B1 | 9/2001 | Choudhary et al. |
| 6,296,686 B1 | 10/2001 | Prasad et al. |
| 6,338,833 B1 | 1/2002 | Aasberg-Petersen |
| 6,361,582 B1 | 3/2002 | Pinnau et al. |
| 6,444,712 B1 | 9/2002 | Janda |
| 6,531,515 B2 | 3/2003 | Moore, Jr. et al. |
| 6,656,346 B2 | 12/2003 | Ino et al. |
| 6,743,961 B2 | 6/2004 | Powers |
| 6,787,576 B2 | 9/2004 | Kiss et al. |
| 6,830,596 B1 | 12/2004 | Deckman et al. |
| 6,896,717 B2 | 5/2005 | Pinnau et al. |
| 6,960,235 B2 | 11/2005 | Morse et al. |
| 6,979,757 B2 | 12/2005 | Powers |
| 7,019,187 B2 | 3/2006 | Powers |
| 7,022,165 B2 | 4/2006 | Paglieri et al. |
| 7,025,941 B1 | 4/2006 | Autenrieth et al. |
| 7,045,554 B2 | 5/2006 | Raje |
| 7,112,271 B2 | 9/2006 | Jo et al. |
| 7,132,042 B2 | 11/2006 | Genetti et al. |
| 7,182,917 B2 | 2/2007 | Krueger |
| 7,217,304 B2 | 5/2007 | Deckman et al. |
| 7,323,148 B2 | 1/2008 | Shah et al. |
| 7,353,982 B2 | 4/2008 | Li |
| 7,374,664 B2 | 5/2008 | Powers |
| 7,396,449 B2 | 7/2008 | Powers |
| 7,404,889 B1 | 7/2008 | Powers |
| 7,419,584 B2 | 9/2008 | Stell et al. |
| 7,527,661 B2 | 5/2009 | Chellappa et al. |
| 7,550,642 B2 | 6/2009 | Powers |
| 7,642,292 B2 | 1/2010 | Severinsky |
| 7,700,005 B2 | 4/2010 | Inui et al. |
| 7,744,747 B2 | 6/2010 | Halsey |
| 7,772,450 B2 | 8/2010 | Iaccino et al. |
| 7,794,690 B2 | 9/2010 | Abatzoglou et al. |
| 7,858,834 B2 | 12/2010 | Powers |
| 7,871,457 B2 | 1/2011 | Shah et al. |
| 7,906,559 B2 | 3/2011 | Olah et al. |
| 7,959,897 B2 | 6/2011 | Cui et al. |
| 7,972,498 B2 | 7/2011 | Buchanan et al. |
| 7,973,087 B2 | 7/2011 | Kibby et al. |
| 8,043,588 B2 | 10/2011 | Hustad et al. |
| 8,198,338 B2 | 6/2012 | Shulenberger et al. |
| 8,440,729 B2 | 5/2013 | Olah et al. |
| 8,500,859 B2 | 8/2013 | Eisenbeger |
| 8,518,151 B2 | 8/2013 | Tessier et al. |
| 8,563,185 B2 | 10/2013 | Assink et al. |
| 8,585,802 B2 | 11/2013 | Keller |
| 8,597,383 B2 | 12/2013 | Pham et al. |
| 8,726,983 B2 | 5/2014 | Khan |
| 8,828,121 B1 | 9/2014 | He et al. |
| 8,835,517 B2 | 9/2014 | Cheiky et al. |
| 8,900,546 B2 | 12/2014 | Van De Graaf et al. |
| 8,931,347 B2 | 1/2015 | Donzier et al. |
| 9,067,850 B2 | 6/2015 | Abbott et al. |
| 9,079,770 B2 | 7/2015 | Ahmed et al. |
| 9,085,497 B2 | 7/2015 | Jennings |
| 9,090,543 B2 | 7/2015 | Schoedel et al. |
| 9,096,806 B2 | 8/2015 | Abba et al. |
| 9,102,532 B2 | 8/2015 | Iaquaniello et al. |
| 9,126,876 B2 | 9/2015 | de Jong et al. |
| 9,138,718 B2 | 9/2015 | Li et al. |
| 9,181,148 B2 | 11/2015 | Katikaneni et al. |
| 9,228,140 B2 | 1/2016 | Abba et al. |
| 9,242,230 B2 | 1/2016 | Moon et al. |
| 9,249,064 B2 | 2/2016 | Kumar et al. |
| 9,255,230 B2 | 2/2016 | Shafi et al. |
| 9,279,088 B2 | 3/2016 | Shafi et al. |
| 9,284,497 B2 | 3/2016 | Bourane et al. |
| 9,284,502 B2 | 3/2016 | Bourane et al. |
| 9,296,961 B2 | 3/2016 | Shafi et al. |
| 9,328,035 B1 | 5/2016 | Kuhn et al. |
| 9,481,938 B2 | 11/2016 | Shin et al. |
| 9,493,350 B2 | 11/2016 | Morico et al. |
| 9,499,403 B2 | 11/2016 | Al-Muhaish et al. |
| 9,624,913 B2 | 4/2017 | Friesth |
| 9,637,432 B2 | 5/2017 | Chakravarti et al. |
| 9,643,906 B2 | 5/2017 | Zubrin et al. |
| 9,676,678 B1 | 6/2017 | Agee et al. |
| 9,752,080 B2 | 9/2017 | Christensen et al. |
| 9,863,244 B2 | 1/2018 | Donzier et al. |
| 9,952,192 B2 | 4/2018 | Donzier et al. |
| 10,008,730 B2 | 6/2018 | Jamal et al. |
| 10,131,599 B2 | 11/2018 | Olah et al. |
| 10,131,602 B1 | 11/2018 | Gondal et al. |
| 10,160,708 B2 | 12/2018 | Lee et al. |
| 10,161,051 B2 | 12/2018 | Palmore et al. |
| 10,173,145 B2 | 1/2019 | Nishibe et al. |
| 10,283,795 B2 | 5/2019 | Jamal et al. |
| 10,329,677 B2 | 6/2019 | Geioushy et al. |
| 10,357,759 B2 | 7/2019 | D'Souza et al. |
| 10,472,951 B2 | 11/2019 | Donzier et al. |
| 10,478,806 B2 | 11/2019 | Schuetzle et al. |
| 10,527,751 B2 | 1/2020 | Donzier et al. |
| 10,532,961 B2 | 1/2020 | Pan et al. |
| 10,800,716 B2 | 10/2020 | Bhatt |
| 10,953,388 B1 | 3/2021 | Harale et al. |
| 2003/0041519 A1 | 3/2003 | Maruko |
| 2003/0129109 A1 | 7/2003 | Bronicki |
| 2003/0172589 A1 | 9/2003 | Krueger |
| 2003/0175565 A1 | 9/2003 | Noda |
| 2004/0094453 A1 | 5/2004 | Lok et al. |
| 2004/0120889 A1 | 6/2004 | Shah et al. |
| 2005/0045034 A1 | 3/2005 | Paglieri et al. |
| 2005/0109037 A1 | 5/2005 | Deckman et al. |
| 2005/0109821 A1 | 5/2005 | Li |
| 2005/0211603 A1 | 9/2005 | Guillaume et al. |

(56) References Cited

U.S. PATENT DOCUMENTS

| | | |
|---|---|---|
| 2005/0217479 A1 | 10/2005 | Hale et al. |
| 2006/0013759 A1 | 1/2006 | Jiang et al. |
| 2006/0057060 A1 | 3/2006 | Sun et al. |
| 2006/0124445 A1 | 6/2006 | Labrecque et al. |
| 2007/0157517 A1 | 6/2007 | Tsay et al. |
| 2007/0180991 A1 | 8/2007 | Chellappa et al. |
| 2007/0277870 A1 | 12/2007 | Wechsler |
| 2008/0001645 A1 | 1/2008 | Kuroki |
| 2008/0011644 A1 | 1/2008 | Dean et al. |
| 2008/0011645 A1 | 1/2008 | Dean |
| 2008/0033218 A1 | 2/2008 | Lattner et al. |
| 2008/0067077 A1 | 3/2008 | Kodera et al. |
| 2008/0083648 A1 | 4/2008 | Bishop et al. |
| 2008/0194900 A1 | 8/2008 | Bhirud |
| 2008/0277314 A1 | 11/2008 | Halsey |
| 2008/0283445 A1 | 11/2008 | Powers |
| 2009/0050523 A1 | 2/2009 | Halsey |
| 2009/0221723 A1 | 9/2009 | Leviness |
| 2010/0089795 A1 | 4/2010 | Fujiyama et al. |
| 2010/0137458 A1 | 6/2010 | Erling |
| 2010/0193370 A1 | 8/2010 | Olah et al. |
| 2010/0260657 A1 | 10/2010 | Niitsuma et al. |
| 2011/0076225 A1 | 3/2011 | Shah et al. |
| 2011/0083996 A1 | 4/2011 | Shafi et al. |
| 2011/0089378 A1 | 4/2011 | Sato et al. |
| 2011/0114502 A1 | 5/2011 | Cole et al. |
| 2011/0177410 A1 | 7/2011 | Assink et al. |
| 2011/0247500 A1 | 10/2011 | Akhras et al. |
| 2012/0111051 A1 | 5/2012 | Kulkarni et al. |
| 2012/0168154 A1 | 7/2012 | Chinn et al. |
| 2012/0195824 A1 | 8/2012 | Van De Graaf et al. |
| 2012/0258037 A1 | 10/2012 | Pham et al. |
| 2012/0323059 A1 | 12/2012 | Liu et al. |
| 2013/0129610 A1 | 5/2013 | Kale |
| 2013/0172432 A1 | 7/2013 | Fleys et al. |
| 2013/0202517 A1 | 8/2013 | Ayala et al. |
| 2013/0220884 A1 | 8/2013 | Bourane et al. |
| 2013/0233766 A1 | 9/2013 | Shafi et al. |
| 2013/0248419 A1 | 9/2013 | Abba |
| 2013/0256124 A1 | 10/2013 | Rahman et al. |
| 2014/0170061 A1 | 6/2014 | Chaubey et al. |
| 2014/0246399 A1 | 9/2014 | Chiba |
| 2014/0363345 A1 | 12/2014 | Li et al. |
| 2015/0037246 A1 | 2/2015 | Morico et al. |
| 2015/0047986 A1 | 2/2015 | Shin et al. |
| 2015/0231561 A1 | 8/2015 | Reardon et al. |
| 2015/0240717 A1 | 8/2015 | Starcher et al. |
| 2015/0290575 A1 | 10/2015 | Rothermel et al. |
| 2016/0214859 A1 | 6/2016 | Beltramini et al. |
| 2016/0264886 A1 | 9/2016 | Davydov |
| 2016/0340187 A1 | 11/2016 | Said et al. |
| 2017/0050845 A1 | 2/2017 | Lofberg et al. |
| 2018/0066197 A1 | 3/2018 | Koseoglu et al. |
| 2018/0079643 A1 | 3/2018 | Mortensen et al. |
| 2018/0094195 A1 | 4/2018 | Lehoux et al. |
| 2018/0119026 A1 | 5/2018 | Kinzl et al. |
| 2018/0148655 A1 | 5/2018 | Low et al. |
| 2018/0187106 A1 | 7/2018 | Abudawoud et al. |
| 2018/0187107 A1 | 7/2018 | Abudawoud et al. |
| 2018/0312767 A1 | 11/2018 | Al-Sayed et al. |
| 2018/0370796 A1 | 12/2018 | Mokheimer et al. |
| 2019/0003303 A1 | 1/2019 | Donzier et al. |
| 2019/0067706 A1 | 2/2019 | Liu et al. |
| 2019/0112535 A1 | 4/2019 | Kinzl et al. |
| 2019/0135624 A1 | 5/2019 | Mair |
| 2019/0168206 A1 | 6/2019 | Yavuz et al. |
| 2019/0359894 A1 | 11/2019 | Heidel et al. |
| 2019/0376821 A1 | 12/2019 | Donzier et al. |
| 2021/0163832 A1 | 6/2021 | Harale |
| 2021/0163833 A1 | 6/2021 | Harale |
| 2021/0164393 A1 | 6/2021 | Younes |
| 2021/0188633 A1 | 6/2021 | Alsolami et al. |

FOREIGN PATENT DOCUMENTS

| | | |
|---|---|---|
| AU | 2005287034 | 3/2006 |
| AU | 2010291148 | 3/2011 |
| AU | 2012243063 | 10/2012 |
| CA | 2458314 | 4/1999 |
| CA | 2580580 | 3/2006 |
| CA | 2580585 | 3/2006 |
| CA | 2414657 | 5/2011 |
| CA | 2547011 | 8/2011 |
| CA | 2938299 | 5/2015 |
| CN | 203415657 | 1/2014 |
| CN | 104098071 | 10/2014 |
| CN | 104258864 | 1/2015 |
| CN | 102482079 | 5/2016 |
| CN | 105561998 | 5/2016 |
| CN | 103596671 | 6/2016 |
| CN | 103586030 | 11/2016 |
| CN | 105197887 | 3/2017 |
| CN | 105776133 | 11/2017 |
| CN | 110600775 | 12/2019 |
| EP | 0130933 | 9/1987 |
| EP | 0684066 | 11/1995 |
| EP | 0892862 | 1/1999 |
| EP | 1024111 | 8/2000 |
| EP | 1130080 | 9/2001 |
| EP | 1294637 | 3/2003 |
| EP | 1683216 | 7/2006 |
| EP | 1789171 | 5/2007 |
| EP | 1789172 | 5/2007 |
| EP | 1828085 | 9/2007 |
| EP | 1829821 | 9/2007 |
| EP | 2035329 | 3/2009 |
| EP | 0909804 | 9/2010 |
| EP | 2696966 | 2/2014 |
| EP | 2825503 | 1/2015 |
| EP | 2999537 | 3/2016 |
| EP | 2473441 | 8/2018 |
| FR | 2943657 | 3/2009 |
| GB | 2461632 | 12/2009 |
| JP | H 09278403 | 10/1997 |
| JP | 2943657 | 8/1999 |
| JP | 2001348205 | 12/2001 |
| JP | 2004502623 | 1/2004 |
| JP | 2004249264 | 9/2004 |
| JP | 2004352528 | 12/2004 |
| JP | 2005044601 | 2/2005 |
| JP | 2007190455 | 8/2007 |
| JP | 2008513337 | 5/2008 |
| JP | 2008513338 | 5/2008 |
| JP | 4381033 | 10/2009 |
| JP | 2010266155 | 11/2010 |
| JP | 2011195352 | 10/2011 |
| JP | 2011195387 | 10/2011 |
| JP | 2011206612 | 10/2011 |
| JP | 2013503807 | 2/2013 |
| JP | 5390448 | 10/2013 |
| JP | 5588581 | 8/2014 |
| JP | 2014519463 | 8/2014 |
| JP | 5611627 | 9/2014 |
| JP | 2014169222 | 9/2014 |
| JP | 6040701 | 12/2016 |
| JP | 6345406 | 6/2018 |
| KR | 101531291 | 7/2015 |
| KR | 101828938 | 2/2018 |
| NO | 200701530 | 4/2007 |
| NO | 200701532 | 6/2007 |
| TW | 200619136 | 6/2006 |
| TW | 200630158 | 9/2006 |
| WO | WO 2000009633 | 2/2000 |
| WO | WO 2000016901 | 3/2000 |
| WO | WO 2001064577 | 9/2001 |
| WO | WO 2002002460 | 1/2002 |
| WO | WO 2002038703 | 5/2002 |
| WO | WO 2002069430 | 9/2002 |
| WO | WO 2002070402 | 9/2002 |
| WO | WO 2004041714 | 5/2004 |
| WO | WO 2005051590 | 6/2005 |
| WO | WO 2006034086 | 3/2006 |

(56) References Cited

FOREIGN PATENT DOCUMENTS

| | | |
|---|---|---|
| WO | WO 2006034100 | 3/2006 |
| WO | WO 2006034103 | 3/2006 |
| WO | WO 2006037584 | 4/2006 |
| WO | WO 2006082933 | 8/2006 |
| WO | WO 2006097703 | 9/2006 |
| WO | WO 2007031713 | 3/2007 |
| WO | WO 2008000782 | 1/2008 |
| WO | WO 2009073436 | 6/2009 |
| WO | WO 2010009077 | 1/2010 |
| WO | WO 2010009082 | 1/2010 |
| WO | WO 2010009089 | 1/2010 |
| WO | WO 2010017372 | 2/2010 |
| WO | WO 2010107942 | 9/2010 |
| WO | WO 2010109106 | 9/2010 |
| WO | WO 2010143783 | 12/2010 |
| WO | WO 2011026943 | 3/2011 |
| WO | WO 2011063353 | 5/2011 |
| WO | WO 2012006429 | 1/2012 |
| WO | WO 2012142009 | 10/2012 |
| WO | WO 2012143096 | 10/2012 |
| WO | WO 2012158673 | 11/2012 |
| WO | WO 2013137720 | 9/2013 |
| WO | WO 2015128045 | 9/2013 |
| WO | WO 2014170184 | 10/2014 |
| WO | WO 2015128018 | 9/2015 |
| WO | WO 2015183200 | 12/2015 |
| WO | WO 2016069385 | 5/2016 |
| WO | WO 2016193736 | 12/2016 |
| WO | WO 2016207892 | 12/2016 |
| WO | WO 2017001891 | 1/2017 |
| WO | WO 2017085594 | 5/2017 |
| WO | WO 2018142343 | 8/2018 |
| WO | WO 2018142351 | 8/2018 |
| WO | WO 2018226617 | 12/2018 |
| WO | WO 2020118420 | 6/2020 |
| ZA | 201201141 | 10/2012 |

OTHER PUBLICATIONS

U.S. Appl. No. 17/118,075, Al-Rowaili et al., filed Dec. 10, 2020.
U.S. Appl. No. 17/118,115, Al-Rowaili et al., filed Dec. 10, 2020.
U.S. Appl. No. 17/140,258, Younes et al., filed Jan. 4, 2021.
U.S. Appl. No. 17/140,274, Younes et al., filed Jan. 4, 2021.
U.S. Appl. No. 61/562,189, Lee et al., filed Nov. 21, 2011.
IEA, "Putting CO2 to Use: Creating value from emissions," Sep. 2019, 86 pages.
Abbassi et al., "Efficiency improvements in production profiling using ultracompact flow array sensing technology," Petrophysics, Aug. 2018, 59:4 (457-488), 32 pages.
Amo et al., "Low-Quality Natural Gas Sulfur Removal/Recovery," Membrane Technology and Research, DOE Report DE-AC21-92MC28133—01, Jan. 29, 1998, 107 pages.
An et al., "Morphology control of Co2C nanostructures via the reduction process for direct production of lower olefins from syngas," Journal of Catalysis, Oct. 2018, 366:289-99, 11 pages.
Arora and Prasad, "An overview on dry reforming of methane: strategies to reduce carbonaceous deactivation of catalysts," RSC Adv., 2016, 6:108668, 21 pages.
Aschoundong et al., "Silane Modification of Cellulose Acetate Dense Films as Materials for Acid Gas Removal Macromolecules," Macromolecules, Jul. 9, 2013, 46:14, 11 pages.
Belov et al., "Gas transport and free volume in hexafluoropropylene polymers," Journal of Membrane Science, Nov. 2011, 383, 8 pages.
Bernardo et al., "Gas transport properties of Pebax/room temperature ionic liquid gel membranes," Separation and Purification Technology, Sep. 2012, 97, 13 pages.
Bhide et al., "Hybrid processes for the removal of acid gases from natural gas," Journal of Membrane Science, Mar. 4, 1998, 140:1, 2 pages, Abstract Only.
Chatteijee et al., "Poly(ether urethane) and poly(ether urethane urea) membranes with high $H_2S/CH_4$ selectivity," Journal of Membrane Science, Nov. 1997, 135:99, 8 pages.

Chu et al., "Negatively Thermoresponsive Membranes with Functional Gates Driven by Zipper-Type Hydrogen-Bonding Interactions," Angew. Chem. Int. Ed., 2005, 44:2124-2127, 4 pages.
Cimino, "Deploying a solar hybrid technology in a remote oil and gas production site," Journal of the Japan Institute of Energy, Jan. 2015, 94:1163-1168, 7 pages.
Desouza et al., "Portable Emission Measurement System (PEMS) Testing of a 100KVA Generator using Red Diesel and ISO grade Diesel," King's College London, Environmental Research Group, Dec. 2016, 12 pages.
Er-rbib et al., "Dry reforming of methane—review of feasibility studies," Chemical Engineering Transactions, 2012, 29:163-168, 7 pages.
Fakeeha et al., "Effect of changing CH4/CO2 ratio on hydrogen production by dry reforming reaction," 16th WHEC, Jun. 13-16, 2006, 1:245-256, 12 pages.
Fasihi et al., "Techno-economic assessment of CO2 direct air capture plants," Journal of Cleaner Production, Jul. 2019, 224:957-980, 24 pages.
FuelCell Energy "Air Products and FuelCell Energy Begin Construction of High Efficiency Hydrogen Energy Station Demonstration for Combined Hydrogen, Electricity and Heat Generation," System Designed to Address Industrial and Transportation Applications, Mar. 2007, 5 pages.
Goeppert et al., "Air as the renewable carbon source of the future: an overview of CO2 capture from the atmosphere," Energy & Environmental Science, 2012, 5:7833-7853, 21 pages.
Homerenergy.com[online], "Homer Pro 3.14" Jun. 19, 2020, [retrieved on Dec. 28, 2020], retrieved from URL <https://www.homerenergy.com/products/pro/docs/latest/how_homer_creates_the_generator_efficiency_curve.html>, 1 page.
Ibrahim et al., "Dry reforming of methane using Ce-modified Ni supported on 8% PO4 +ZrO2 catalysts," Catalysts, 2020, 10:242, 16 pages.
Jafarbegloo et al., "One-pot synthesis of NiO-MgO nanocatalysts for CO2 reforming of methane: The influence of active metal content on catalytic performance," Journal of Natural Gas Science and Engineering 2015, 27:2 (1165-1173), 23 pages.
Jansen et al., "On the unusual solvent and the effect on the gas transport in perfluorinated Hyflon AD Membranes," Journal of Membrane Science, Jan. 2007, 287:1, 6 pages.
Kang et al., "Effect of copper surface morphology on grain size uniformity of graphene grown by chemical vapor deposition," Current Applied Physics 2019, 19,12:1414-1420, 7 pages.
Keith et al., "A Process for Capturing $CO_2$ from the Atmosphere," Joule, Aug. 2018, 23 pages.
Kim et al., "Methanol synthesis from syngas over supported palladium catalysts prepared using water-in-oil microemulsion," Applied Catalysis A: General, 1998, 169:157-64, 8 pages.
Knipe et al., "CO2 Absorption and Regeneration Cycling with Micro-Encapsulated CO2 Sorbents," Environmental Science & Technology, Feb. 2018, 24 pages.
Kraftschik et al., "Dense film polyimide membranes for aggressive sour gas feed separations," Journal of Membrane Science, Feb. 1, 2013, 428, 12 pages.
Lallemand et al., "Extending the treatment of highly sour gases: cryogenic distillation," Digital Refining: Processing, Operations & Maintenance, Jan. 2014, 8 pages.
Lallemand et al., "Highly sour gas processing: Bulk removal with SPREX Process," IPTC-10581-MS, International Petroleum Technology Conference, Nov. 2005, 18 pages.
Lallemand et al., "Solutions for the treatment of highly sour gases," Digital Refinding: Processing, Operations & Maintenance, Apr. 2012, 14 pages.
Lavoie, "Review on dry reforming of methane, a potentially more environmentally friendly approach to increasing natural gas exploitation," Frontier in Chemistry, Nov. 2014, 2:81, 17 pages.
Leo, "Tri-Generation Fuel Cells: Opening Doors to Distributed Hydrogen Markets," CryoGas International, Jul. 2016, 3 pages.
Lockhart, "Sour oil and gas management: 3.3," vol. Lii/New Developments: Energy, Transport, Sustainability Encyclopedia of Hydrocarbons, 2007, 34 pages.

(56) References Cited

OTHER PUBLICATIONS

Lokhandwala et al., "Membrane separation of nitrogen from natural gas: A case study from membrane synthesis to commercial deployment," Journal of Membrane Science, Jan. 2010, 346, 10 pages.

Malico et al., "Design of a trigeneration system using a high-temperature fuel cell," International journal of energy research, Special Issue: The changing energy paradigm, challenges and new developments, Feb. 2009, 33:2 (144-151), 8 pages.

Manliclic et al., "Tri-Generation Fuel Cell Technologies for Location-Specific Applications," AN047, Advanced Power and Energy Program, Jun. 17, 2014, 19 pages.

Merkel and Toy, "Comparison of Hydrogen Sulfide Transport Properties in Fluorinated and Nonfluorinated Polymers," Macromolecules, Sep. 2006, 39:22, 10 pages.

Milanov et al., "Dry Reforming of Methane with CO2 at Elevated Pressures," New Technologies and Alternative Feedstocks in Petrochemistry and Refining DGMK Conference Oct. 9-11, 2013, 5 pages.

Mogensen et al., "Methane Steam Reforming over an Ni-YSZ Solid Oxide Fuel Cell Anode in Stack Configuration," Journal of Chemistry, 2014, Article ID 710391, 9 pages.

Mori et al., "Reactor configuration and concentration polarization in methane steam reforming by a membrane reactor with a highly hydrogen-permeable membrane," Industrial & Engineering Chemistry Research, Feb. 2007, 46:7 (1952-1958), 7 pages.

Oi et al., "Simulation and cost comparison of CO2 liquefaction," Energy Procedia, 2016, 86:500-510, 11 pages.

Olah et al., "Single step Bi-reforming and oxidative Bi-reforming of methane (Natural gas) with Steam and Carbon dioxide to Metgas for methanol synthesis," ACS publications, 2015, 18 pages.

Park et al., "Reversible Self-Actuated Thermo-Responsive Pore Membrane," Scientific Report, Dec. 2016, 10 pages.

Perez-Fortes et al., "Design of a Pilot SOFC System for the Combined Production of Hydrogen and Electricity under Refueling Station Requirements," Fuel Cells, 2019, 19:4 (389-407), 19 pages.

Pitchaimani et al., "Manufacturable plastic microfluidic valves using thermal actuation," Lab on a Chip, Aug. 2009, 9:21 (3082-3087), 6 pages.

Qin et al., "Roughness of copper substrate on three-dimensional tin electrode for electrochemical reduction of CO2 into HCOOH," Journal of $CO_2$ Utilization, 2017, 21:219-223, 5 pages.

Robeson, "The upper bound revisited," Journal of Membrane Science, 320, Jul. 15, 2008, 11 pages.

Rufford et al., "The removal of CO2 and N2 from natural gas: A review of conventional and emerging process technologies," Journal of Petroleum Science and Engineering, Sep. 2012, 94-95, 32 pages.

Schakel et al., Assessing the techno-environmental performance of CO2 utilization via dry reforming of methane for the production of dimethyl ether,: Journal of CO2 utilization, Dec. 2016,16:138-149, 12 pages.

Schulz et al., "Dry Reforming of Methane at Elevated Pressures," New Technologies and Alternative Feedstocks in Petrochemistry and Refining DGMK Conference Oct. 9-11, 2013, Dresden, Germany, DGMK—Tagungsbericht 2013-2, 1 page.

Shi et al., "An Introduction of CO2 Conversion by Dry Reforming with Methane and New Route of Low-Temperature Methanol Synthesis," Accounts of Chemical Research, 2013, 46:1838-47, 10 pages.

Shojaeddini, "Oil and gas company strategies regarding the energy transition," Progress in Energy, 01:2001, 2019, 20 pages.

Su et al., "Syngas to light olefins conversion with high olefin/paraffin ratio using ZnCrOx/AlPO-18 bifunctional catalysts," Nature Communications, Mar. 2019, 10:1, 8 pages.

Uemoto et al., "Electrochemical Carbon Dioxide Reduction in Methanol at Cu and Cu2O—Deposited Carbon Black Electrodes," ChemEngineering 3.1:15, 2019, 10 pages.

Vericella et al., "Encapsulated liquid sorbents for carbon dioxide capture," Nature Communications, Feb. 2015, 7 pages.

Wang et al., "CO2 capture by solid adsorbents and their application: current status and new trends," Energy & Environmental Science, 2011, 4:42-55, 14 pages.

Wang et al., "One-step synthesis of dimethyl ether from syngas on ordered mesoporous copper incorporated alumina," Journal of Energy Chemistry, Sep. 2016, 5:775-81, 7 pages.

Weiss et al., "Coking of Oil Sands, Asphaltenes and Residual Oils in the LR-Process," Unitar Conference, Aug. 9, 1988, 23 pages.

Wismann et al., "Electrified methane reforming: A compact approach to greener industrial hydrogen production," Science Magazine, May 2019, 364:6442 (756-759), 12 pages.

Wolfbeisser et al., "Methane dry reforming over ceria-zirconia supported Ni catalysts," Catal Today, Nov. 15, 2016, 277:2, 12 pages.

Xu et al., "An Improved CO2 Separation and Purification System Based on Cryogenic Separation and Distillation Theory," Energies ISSN 1996-1073, May 2014, 7: 3484-3502.

Yu et al., "Combined Hydrogen, Heat and Power (CHHP) pilot plant design," International Journal of Hydrogen Energy, Apr. 22, 2013, 38:12 (4881-4888), 8 pages.

Zhang et al., "Coke-resistant Ni@SiO2 catalyst for dry reforming of methane," Applied Catalysis B: Environmental, Oct. 2015, 176-177: 513-521, 9 pages.

\* cited by examiner

400

OLEFIN PRODUCTION VIA DRY REFORMING AND OLEFIN SYNTHESIS IN A VESSEL

TECHNICAL FIELD

This disclosure relates to dry reforming of methane and olefin synthesis.

BACKGROUND

Low molecular-weight saturated hydrocarbons, such as methane, ethane, and butane, may be feedstocks to generate products including intermediate products. A source of these low molecular-weight saturated hydrocarbons may be natural gas processing plants.

Ethane, propane, and butane may be subjected to steam cracking to generate olefins including, for example, ethylene, propylene, and butadiene. These olefins are produce primarily through this steam cracking. Ethylene and propylene are significant sources of industrial chemicals and plastics products including polyolefins and other polymers. Butadiene is used in making synthetic rubber.

Methane, which may be labeled as the simplest hydrocarbon, may be subjected to steam reforming to generate synthetic gas (syngas) that includes hydrogen ($H_2$) and carbon monoxide (CO). The hydrogen may be separated from the syngas to produce hydrogen. The syngas may be distributed including to different facilities to make ammonia or methanol. The syngas may be transported to a facility having a Fischer Tropsch (FT) reactor that converts the syngas into FT liquid/wax products.

Carbon dioxide is the primary greenhouse gas emitted through human activities. Carbon dioxide ($CO_2$) may be generated in various industrial and chemical plant facilities. At such facilities, the utilization of $CO_2$ as a feedstock may reduce $CO_2$ emissions at the facility and therefore decrease the $CO_2$ footprint of the facility. The conversion of the greenhouse gas $CO_2$ into value-added feedstocks or products may be beneficial.

SUMMARY

An aspect relates to a method of producing olefin via dry reforming and olefin synthesis, the method including providing feed including methane and carbon dioxide to a vessel, converting methane and carbon dioxide in the vessel into syngas (that includes hydrogen and carbon monoxide) via dry reforming in the vessel, and cooling the syngas via a heat exchanger in the vessel. The method includes synthesizing olefin from the syngas in the vessel, wherein the olefin includes ethylene, propylene, or butene, or any combinations thereof. The method includes discharging the effluent from the vessel, the effluent including the olefin.

Another aspect includes a method of producing olefin, including converting (involving dry reforming) methane and carbon dioxide via a dry reforming catalyst in a dry reforming section in a reactor vessel into syngas that includes hydrogen and carbon monoxide. The method includes flowing the syngas from the dry reforming section through a heat exchange section in the reactor vessel to cool the syngas with a cooling medium in the heat exchange section. The method includes flowing the syngas as cooled from the heat exchange section to an olefin synthesis section in the reactor vessel. The method includes synthesizing olefin from the syngas via an olefin synthesis catalyst in the olefin synthesis section, wherein the olefin includes ethylene, propylene, or butene, or any combinations thereof.

Yet another aspect is an olefin production system including a reactor vessel having a feed inlet to receive a feed including methane and carbon dioxide. The reactor vessel has a dry reforming section (having a dry reforming catalyst) in the reactor vessel to convert the methane and the carbon dioxide into syngas that includes hydrogen and carbon monoxide. The reactor vessel has a heat exchange section (having a heat exchanger) in the reactor vessel to receive the syngas from the dry reforming section and cool the syngas with a cooling medium. The reactor vessel includes an olefin synthesis section (having an olefin synthesis catalyst) in the reactor vessel to synthesize olefin from the syngas and discharge an effluent including the olefin from the reactor vessel, wherein the olefin comprises ethylene, propylene, butene, or any combinations thereof.

The details of one or more implementations are set forth in the accompanying drawings and the description below. Other features and advantages will be apparent from the description and drawings, and from the claims.

DETAILED DESCRIPTION

Some aspects of the present disclosure are directed to olefin generation from carbon dioxide and methane in a vessel (a reactor vessel). Carbon dioxide and methane may be fed to the vessel. The olefin generated in the vessel may discharge from the vessel. The olefin synthesis may be via dry reforming of the methane in the vessel. In particular, the olefin may be synthesized from the synthetic gas (syngas) generated by the dry reforming. The dry reforming and the olefin synthesis may occur in the same vessel. Advantages of performing the dry reforming, heat exchange (cooling), and olefin synthesis in the same vessel may include a more compact system, smaller footprint, capital cost reduction, improved heat management in operation, and so forth.

Dry reforming may be beneficial for consuming the two-greenhouse gases methane ($CH_4$) and carbon dioxide ($CO_2$). Dry reforming is a process that may react $CH_4$ with $CO_2$ to produce syngas with the aid of catalyst. The syngas may include hydrogen ($H_2$) and carbon monoxide (CO). The dry reforming reaction may be characterized as $CH_4 + CO_2 \rightarrow 2H_2 + 2CO$.

Aspects may include olefin production by performing both dry reforming and olefin synthesis in the same vessel. Thus, embodiments of the present techniques include a reactor for olefin synthesis via dry reforming, and in which both the dry reforming reaction and the olefin synthesis reaction occur in the same reactor vessel. In certain embodiments, the reactor (reactor vessel) may have at least three sections including a dry reforming section, a heat exchanger section, and an olefin synthesis section. The reactor converts carbon dioxide and methane into olefin in the vessel of the reactor.

Due to the mounting concerns about climate change, CCUS (carbon capture, utilization, and storage) is a focus of research and development around the world. The utilization can include conversion. $CO_2$ conversion technologies have attracted attention at least because of difficulties associated with geological storage of $CO_2$. An aim of $CO_2$ conversion may be to utilize concentrated $CO_2$ (e.g. from $CO_2$ capture) as a feedstock to produce valuable chemicals via various conversion processes.

In implementations herein, dry reforming of $CH_4$ is a $CO_2$ conversion technology for mitigating $CO_2$ emissions. The dry reforming of methane (DRM) has relatively high $CO_2$ utilization ratio (e.g., molar ratio $CH_4:CO_2=1:1$) and thus may facilitate $CO_2$ reduction. The dry reforming of $CH_4$ may also reduce emissions of $CH_4$, which like CO2, is a greenhouse gas.

Embodiments herein utilize $CO_2$ as feedstock via DRM to produce olefins. As presented herein in embodiments, the syngas produced from DRM is utilized directly in olefin production. Again, the syngas produced from DRM may be primarily $H_2$ and CO at a molar ratio of 1:1 based on the ideal thermodynamic equilibrium.

Figure 1:
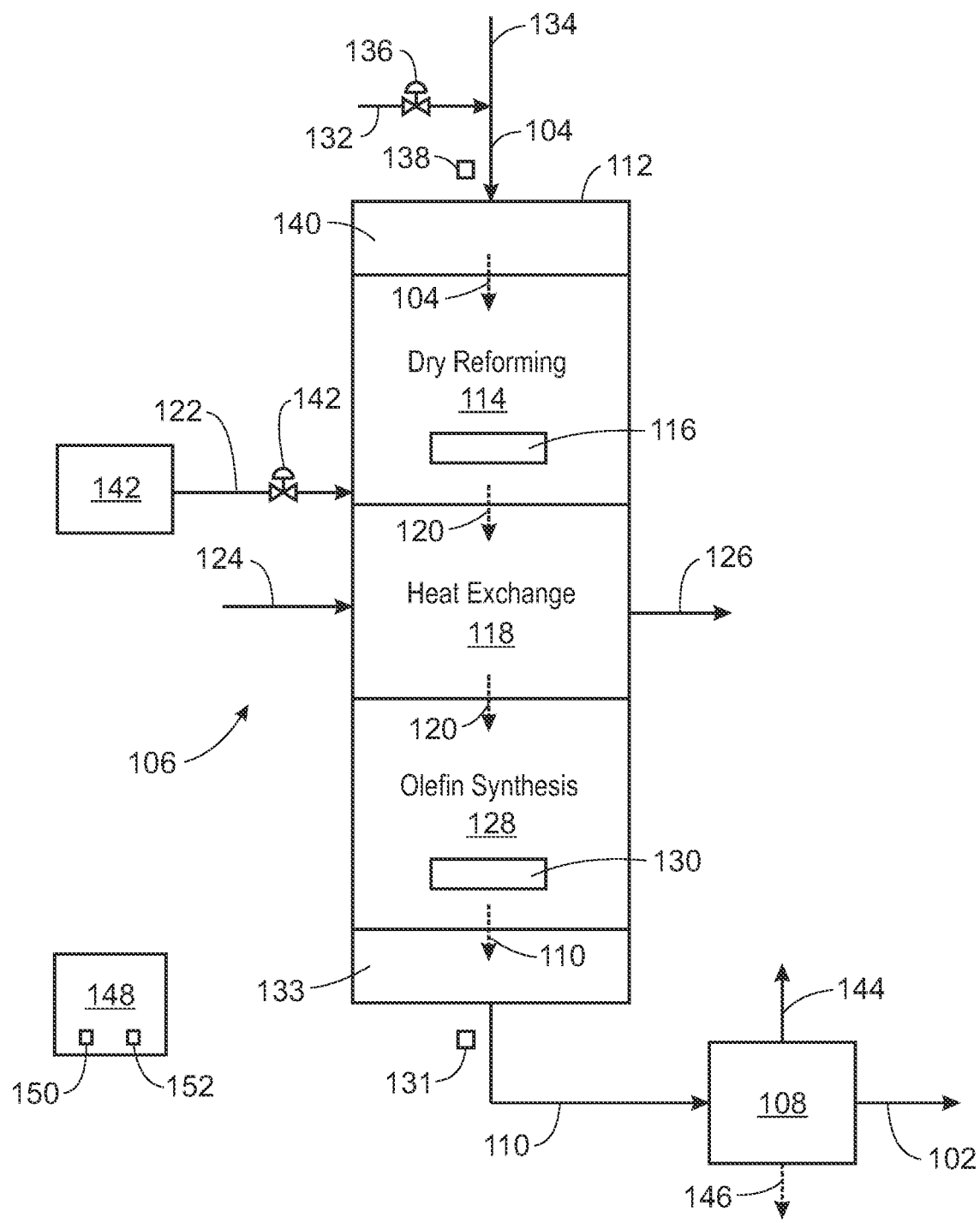
FIG. 1 is a diagram of a system that produces olefin.

FIG. 1 is a system 100 that produces olefin 102 (alkene), such as ethylene, propylene, or butene. The feed 104 includes $CO_2$ and $CH_4$. Advantageously, utilization of $CO_2$ as feed can reduce $CO_2$ emissions (the $CO_2$ footprint) at a facility. In implementations, the $CH_4$ may be fed in a methane-rich stream, such as natural gas. Utilization of $CH_4$ as feed can reduce $CH_4$ emissions at a facility.

The system 100 includes a reactor 106, as well as a downstream system 108 that processes effluent 110 from the reactor 106 to give the olefin 102 product. The reactor 106 may generally be a continuous reactor. The system 100 may generally be a continuous system.

The reactor 106 includes a reactor vessel 112 having sections (zones or portions) for performing multiple respective unit operations. In implementations, the three sections (dry reforming, heat exchange, and olefin synthesis) discussed below are all generally in the interior of the vessel 112 to the inside of the vessel 112 wall.

The reactor vessel 112 may be metal, such as stainless steel. The reactor vessel 112 may have a vertical orientation as depicted, or may have a horizontal orientation. In implementations, the vessel 112 may have elliptical heads. The reactor vessel 112 may have nozzles (e.g., flanged, threaded, etc.) at inlets and outlets for coupling to inlet supply conduits and outlet discharge conduits.

The reactor vessel 112 may have vessel internals (e.g., plates, perforated plates, conduits, distributors, baffles, etc.) to provide for and accommodate the division or segregation of the vessel 112 into multiple sections. The three sections (parts) might be structurally separate in the vessel via, for example, divider plate or divider meshes. Flow occurs from one section to another section. Divider plates, if employed, may have holes. Distributers may also be employed to facilitate and distribute flow. These and other vessel internals may be, for example, a stainless steel, a Hastelloy®, or an Inconel®, and the like.

The reactor 106 may be a "single" reactor for performing multiple operations and be labeled colloquially as a "single-step" reactor in performing multiple unit operations or steps contemporaneously (or simultaneously) in the same vessel 112.

In the illustrated embodiment, the reactor 106 is configured to perform two different reactions of dry reforming and olefin synthesis contemporaneously in two respective sections, as discussed below. While the olefin synthesis within the vessel 112 may be in sequence downstream of the dry reforming within the vessel 112, the two reactions may occur as the same time in the continuous operation of the reactor 106.

The reactor 106 includes a dry reforming section 114 to perform (via reforming catalyst 116) the dry reforming reaction represented by $CH_4+CO_2\rightarrow 2H_2+2CO$. The dry reforming section 114 may be labeled as a dry reforming zone, dry reforming part, dry reformer, etc. The dry reforming section 114 may be enclosed within the reactor vessel 112 of the reactor 106. The dry reforming section 114 has dry reforming catalyst 116 to convert $CH_4$ and $CO_2$ of the feed 104 into synthetic gas (syngas). The generated syngas includes $H_2$ and CO. The dry reforming catalyst 116 may be a fixed bed of catalyst in the dry reforming section 114. In certain implementations, the dry reforming catalyst 116 is a nickel-based catalyst. The dry reforming can be conducted, for example, at less than 850° C., less than 800° C., in the range of 700° C. to 900° C., in the range of 750° C. to 875° C., or in the range of 800° C. to 850° C. The molar ratio of the $CO_2$ and $CH_4$ in the feed 104 to the dry reforming section 114 can vary, for example, in the range of 1:1 to 3:1. As can be seen from the above dry-reforming reaction equation, the molar ratio of $H_2$ to CO in the generated syngas is 1:1 based on the ideal thermodynamic equilibrium, but in practice can be different from 1:1. The produced syngas is generally $H_2$ and CO, and the molar ratio of $H_2$ to CO in the syngas is ideally 1 but in practice can be, for example, in the range of 0.4 to 1.

Moreover, as the dry reforming reaction is generally endothermic, heat may be added to the dry reforming section 114. For instance, electrical heaters may be associated with the dry reforming section 114, or the reactor vessel 112 may have a vessel jacket at the dry reforming section 114 for a heat transfer fluid (as a heating medium).

The reactor 106 includes a heat exchange section 118 that may be labeled as a heat exchange zone, heat exchange part, heat exchanger zone, heat exchanger portion, heat exchanger, etc. The heat exchanger is generally disposed within the vessel 112. The heat exchange section 118 may be enclosed within the reactor vessel 112 of the reactor 106. A purpose of the heat exchange section 118 may be to cool the syngas 120 to a desired temperature for feed to the olefin synthesis.

In operation, the heat exchange section 118 cools the syngas 120 discharged from the dry reforming section 114. In some implementations, the syngas 120 can include additional $H_2$ added to increase the molar ratio of $H_2$ to CO in the syngas 120. The heat exchange section 116 utilizes a cooling medium to cool the syngas 120. The cooling medium may be, for example, water such as cooling tower water. The cooling medium may flow through the heat exchange section 116 without change in composition and absorb heat from the syngas 120.

In operation, the cooling medium supply 124 enters the heat exchange section 116. The reactor vessel 112 may have a cooling-medium inlet (e.g., inlet nozzle) coupled to a supply conduit conveying the cooling medium supply 124 to the reactor vessel 112. The cooling medium return 126 discharges from the heat exchange section 116. The reactor vessel 112 may have a cooling-medium outlet (e.g., outlet nozzle) coupled to a return conduit conveying the cooling medium return 126 to the cooling medium system.

With the cooling medium cooling (absorbing heat from) the syngas 120, the cooling medium return 126 has a greater temperature than the cooling medium supply 124. Heat transfer occurs from the syngas 120 to the cooling medium. The cooling medium supply 124 may be, for example, less than 25° C. The cooling medium return 126 may be, for example, at least 100° C. The heat exchange section 118 may be, for example, a shell-and-tube heat-exchanger type or configuration in which tubes are situated in the heat exchange section 118. The heat exchange section 118 can be configured to flow the cooling medium through the tubes, and flow the syngas 120 external to the tubes. On the other hand, the heat exchange section 118 can be configured to flow the syngas 120 through the tubes, and flow the cooling medium external to the tubes. Other heat exchange or heat exchanger configurations are applicable.

The reactor 106 includes an olefin synthesis section 128 that may be labeled as an olefin synthesis zone, olefin synthesis portion, olefin synthesis reactor, olefin reactor, etc. The olefin synthesis section 128 may be enclosed within the reactor vessel 112 of the reactor 106. The olefin synthesis section 128 receives the cooled syngas 120 discharged from the heat exchange section 118. The olefin synthesis section 128 has an olefin synthesis catalyst 130 to convert the syngas 120 to olefin (e.g., olefin 102). The olefin synthesis catalyst 130 may be, for example, a zinc chromium oxide (ZnCrOx)-based catalyst. Other catalysts are applicable.

In general, the residence time in the dry reforming section 114 (dry reforming reaction) and in the olefin synthesis section 128 (olefin synthesis reaction) may be similar. However, the residence time in the olefin synthesis section 128 may be adjusted, for example, by injecting hydrogen after the dry reforming section 114, by changing the catalyst 130 volume (amount), and the like.

The olefin synthesis can be conducted at a temperature in a range of 250° C. to 450° C., or in a range of 290° C. to 410° C., and at a pressure, for example, in a range of 10 bars to 50 bars. The unit bar as used herein is bar absolute (bara). The ZnCrOx based catalyst can be used for olefin synthesis, and the $H_2$:CO feed molar ratio for olefin synthesis can be varied in the range of 1:1 to 2:1. In some instances, to optimize (increase) the feed $H_2$/CO ratio, extra $H_2$ produced by water ($H_2O$) electrolysis utilizing renewable power sources can be injected.

The olefin 102 synthesized may be lower or lighter olefins (4 carbons or less), such as ethylene (C2=), propylene (C3=), or butene (C4=), or any combinations thereof. The butene may include one or more of the four isomers of butene. This olefin 102 (e.g., a mixture of C2=, C3=, and C4=) in the effluent 110 may discharge from the olefin synthesis section 118. If desired, the favoring of C2=, C3=, or C4=generated for the olefin 102 mixture may involve selection of the catalyst 130 type or specific catalyst 130, control of the operating conditions (e.g., temperature, pressure, etc.), the controlled amount of $CO_2$ in the feed, and the controlled molar ratio of $H_2$ to CO in the syngas 120. Yet, in implementations, the relative amounts of C2=, C3=, and C4= of the olefin 102 may not be crucial. In other words, in those implementations, C2=, C3=, and C4=(including the four isomers of C4=) can collectively be a product or products.

In some implementations, an online analytical instrument 131 (e.g., an online gas chromatograph instrument) may be disposed along the discharge conduit from the reactor vessel 112 to measure composition of the effluent 110. In some implementations, the control system 148 in response to the effluent 110 composition as measured by the online analytical instrument 131, may automatically adjust: (1) flow rate of the carbon dioxide 132 stream (see below), (2) flow rate of the hydrogen 122 (see below), or (3) other operating conditions of the reactor 106.

In some implementations, the reactor vessel 112 may include a discharge portion 133 to facilitate discharge of the effluent 110 of the reactor 106. In other implementations, there is no independent discharge portion 133, and the effluent 110 of the reactor 106 instead discharges generally directly from the olefin synthesis section 128.

The olefin synthesis reaction in the olefin synthesis section 128 that converts the syngas 120 to olefin 102 is generally exothermic. Therefore, the reactor vessel 112 at the olefin synthesis section 128 may have a vessel jacket for a heat-transfer fluid that is a cooling medium (e.g., cooling water). The reactor vessel 112 may have cooling coils (internally in the reactor vessel 112 at the olefin synthesis section 128) that route a cooling medium. To cool the reaction mixture and control temperature of the olefin synthesis section 128, heat transfer may occur from the reaction mixture in the olefin synthesis section 128 to the cooling medium in the reactor vessel jacket or in the cooling coils.

In the illustrated embodiment, carbon dioxide 132 is added to methane 134 to give the feed 104 for introduction to the reactor vessel 112. The carbon dioxide 132 stream may be, for example, at least 90 percent (%) of $CO_2$ by volume (vol %) or on a molar basis (mol %). The methane 134 stream may be a methane-rich stream (e.g., at least 60 vol % $CH_4$), such as natural gas, or a process stream or waste stream having $CH_4$. The flow rate of the carbon dioxide 132 stream and/or the methane 134 stream may be controlled to give a desired or specified percent concentration (e.g., vol % or mol %) of $CO_2$ in the feed 104 or a specified molar ratio of $CO_2$ to $CH_4$ in the feed 104. For example, the molar ratio of $CO_2$ to $CH_4$ in the feed 104 may be specified in the range of 1:1 to 3:1. In implementations, the amount of $CO_2$ in the feed 104 is in the range of 30 vol % to 70 vol %, or at least 40 vol %. In the illustrated implementation, the system 100 includes a control valve 136 (e.g., flow control valve) to control (including adjusting) the flow rate of the carbon dioxide 132 stream to give the specified percent (e.g., at least 40 vol %) of $CO_2$ in the feed 104 or the specified molar ratio (e.g., at least 1) of $CO_2$ to $CH_4$ in the feed 104. In implementations, the volume percent or molar percent of each of $CO_2$ and $CH_4$ in the feed 104 can be calculated based on the known flow rates and compositions of the carbon dioxide 132 steam and methane 134 stream. In one embodiment, an online analyzer instrument 136 (e.g., online gas chromatograph instrument) disposed along the conduit conveying the feed 104 measures the amounts (e.g., in volume percent) of each of $CO_2$ and $CH_4$ in the feed 104.

In some implementations, the control system 148 may automatically adjust the set point of the control valve 136 in response to the composition of the feed 104 as calculated by the control system 148 or as measured by the online analyzer instrument 138. A human operator or user may enter into the control system 148 a specified value (a set point of a master controller) related to the amount of $CO_2$ in the feed 104, such as for the specified concentration of $CO_2$ in the feed or for the specified molar ratio of $CO_2$ to $CH_4$ in the feed 104. To maintain this entered set point (of the master controller), the master controller may direct the flow controller (FC) of the flow control valve 136 as a slave controller. In particular, the master controller may specify a slave set point (e.g., volume flow rate of $CO_2$ 132 stream or mass flow rate of $CO_2$ 132 stream) of the FC for the control valve 136 to give the desired set point of the master controller.

The feed 104 may be introduced to an inlet portion 140 of the reactor vessel 112 to facilitate introduction of the feed 104 into the dry reforming section 114. In other implementations, the feed 104 the reactor vessel 112 does not include an independent inlet portion 140, and the feed 104 is instead introduced generally directly into the dry reforming section 114. In some embodiments, the carbon dioxide 132 and methane 134 may be added in two respective separate streams to the reactor vessel 112 via two respective inlets of the reactor vessel 112.

In implementations, as mentioned, the molar ratio of $H_2$ to CO in the syngas 120 as generated by the dry reforming section 114 may generally be approximated at the ideal ratio of 1 for the ideal thermodynamic equilibrium or stoichiometric relationship for the dry reforming reaction in the dry reforming section 114. In practice, the molar ratio of $H_2$ to CO in the syngas 120 as generated by the dry reforming section 114 may be, for example, in the range of 0.4:1 to 1:1. In implementations, the molar ratio of $H_2$ to CO in the syngas 120 may be estimated based on, for example, the relative amounts of $CO_2$ and $CH_4$ in the feed 104, the operating conditions (e.g., pressure, temperature, etc.) of the dry reforming section 114, the condition of the dry reforming catalyst 116, and so forth. Again, in certain embodiments, the molar ratio of $H_2$ to CO in the syngas 120 as generated by the dry reforming section 114 is in the range of 0.4 to 1. The hydrogen 122 (hydrogen gas $H_2$) may be added to increase this molar ratio to greater than 1, such as in the range of 1 to 2 or 1.1 to 2, or at least 1.1 or at least 1.2. In certain implementations, an online analytical instrument (e.g., online gas chromatograph instrument) is disposed along the reactor vessel 112 to sample the syngas 120 (e.g., as cooled in the heat exchange section 118) to measure the composition of the syngas 120 (with or without the addition of the hydrogen 122) to give a measured value of the molar ratio of $H_2$ to CO in the syngas 120.

A source 142 of hydrogen provides the hydrogen 122 that is added to the reactor vessel 112 to increase the molar ratio of $H_2$ to CO in the syngas 120. The olefin synthesis in the olefin synthesis section 128 may benefit, for example, with the syngas 120 having a molar ratio of $H_2$ to CO of at least 1, or at least 1.1. The hydrogen 122 may be injected not only to adjust the molar ratio of the $H_2$/CO, but also to reduce the temperature of the syngas 120. The injected hydrogen 122 may cool the syngas 120.

In implementations, the flow rate of the hydrogen 122 may be controlled (including adjusted) by a control valve 142 (e.g., flow control valve) to give the desired or specified molar ratio of $H_2$ to CO in the syngas 120. In the illustrated embodiment, the addition of the hydrogen 122 is depicted at the discharge portion of the dry reforming section 114. However, the hydrogen 122 may also be added to the heat exchange section 118 or at the introduction of the syngas 120 (as cooled in the heat exchange section 118) to the olefin synthesis section 128.

In certain implementations, the source 142 of hydrogen 122 is a water electrolysis unit. Electrolysis of water is the decomposition of water into oxygen and hydrogen gas due to the passage of an electric current. The water electrolysis unit may include at least one water-electrolysis electrochemical cell (electrolytic cell) having a pair of electrodes immersed in water. An electrolyte (e.g., sulfuric acid, potassium hydroxide, sodium hydroxide, etc.) may be added to the water. The pair of electrodes are a cathode and an anode. The cathode and anode may each be an inert metal, such as platinum, stainless steel, iridium, etc. In operation, an electric current may be provided to the cathode. The electrolysis of water may receive energy to overcome activation barriers. In implementations, energy for the electrolysis of water in the water electrolysis unit may be provided via renewable sources, such as energy sources relying on wind or solar.

In the electrochemical cell of the water electrolysis unit, reduction of the water at the cathode generates $H_2$. Oxidation of water at the anode generates oxygen gas ($O_2$). The $H_2$ and $O_2$ may be collected separately. The overall equation of the decomposition of the water in the electrolytic cell can be: $2\ H_2O \rightarrow 2\ H_2 + O_2$. Therefore, the number of hydrogen molecules generated may be twice the number of oxygen molecules generated. The electrolysis of water via the water electrolysis unit may produce $H_2$ and $O_2$ at a $H_2/O_2$ molar ratio of 2 to 1. The number of electrons through the water can be at least twice the number of generated hydrogen molecules and four times the number of generated oxygen molecules.

As indicated, hydrogen 122 produced from the water electrolysis unit can be added to the syngas 120 to adjust the molar ratio of $H_2$ to CO in the syngas 120. As mentioned for some implementations, a flow control valve 142 disposed along the conduit conveying the hydrogen 122 modulates the amount of hydrogen 122 added to give the desired or specified molar ratio of $H_2$ to CO in the syngas 120. Again, the desired molar ratio may be specified based on the desired molar ratio of $H_2$ to CO for the olefin synthesis. The addition of the hydrogen 122 may increase the $H_2$:CO molar ratio, for example, to between 1 to 2.

If needed, a hydrogen mechanical compressor can be disposed along the conduit conveying the hydrogen 122. The hydrogen compressor can provide motive force for flow (addition) of the hydrogen 122 into the reactor vessel 112.

In some implementations, the control system 148 may automatically adjust the set point of the control valve 142 in response to the composition of the syngas 120 as calculated by the control system 148 or as measured by an online analyzer instrument. A human operator or user may enter into the control system 148 a specified value (a set point of a master controller) for the molar ratio of $H_2$ to CO in the syngas 120. To maintain this entered set point (of the master controller), the master controller may direct the flow controller (FC) of the flow control valve 142 as a slave controller. In particular, the master controller may specify a slave set point (e.g., volume flow rate of hydrogen 122 or mass flow rate of hydrogen 122) of the FC for the control valve 142 to give the desired set point of the master controller.

The effluent 110 discharged from the reactor 106 includes the olefin 102 generated in the olefin synthesis section 128. The olefin 102 may generally be light olefins. The olefin 102 may be a mixture of light olefins. The olefin 102 may be a mixture of ethylene, propylene, and butene. In addition to the olefin 102, the effluent 110 may include $H_2$, CO, and $CO_2$. The amount, e.g., mole percent (mol %), of $CO_2$ in the effluent 104 may be correlative with (e.g., directly proportional with) the amount of $CO_2$ in the feed 104, or correlative with (e.g., directly proportional with) with the molar ratio or volume ratio of $CO_2$ to $CH_4$ in the feed 104. In implementations, the effluent 104 may include more $H_2$ than $CO_2$ and more CO than $CO_2$. In certain implementations, the effluent 110 can include unreacted $CH_4$, such as when the conversion of the $CH_4$ of the feed 104 less than 100% in the reactor 106 (including in the dry reforming section 114). In one implementation, the effluent 110 includes a trace amount (e.g., less than 0.1 mol %) of $CH_4$.

Lastly, the effluent 110 can include a relatively small amount of hydrocarbon (e.g., C5+) other than (e.g., heavier than) the olefin 102, and in which this hydrocarbon may generally have five carbons or more. The amount of these heavier hydrocarbons (C5+) in the effluent 110 is significantly less than the amount of olefin 102 in the effluent 104, e.g., least 95% less on a mole basis and at least 87% less on a weight (mass) basis. The amount of hydrocarbons in addition to the olefin 102 in the effluent 110 can be influenced by the molar (volume) ratio of $CO_2$ to $CH_4$ in the feed 104. In implementations, the amount of hydrocarbons other than the olefin 102 in the effluent 110 is correlated inversely (e.g., inversely proportional) with the molar ratio of $CO_2$ to $CH_4$ in the feed 104.

As mentioned, the effluent 110 of the reactor 106 may discharge from the reactor vessel 112 to a downstream system 108 for processing the effluent 110. The downstream system 108 may a separation system to remove components 144 from the effluent 110 to give the product olefin 102. The components 144 may include, for example, $H_2$, CO, $CO_2$, and any unreacted $CH_4$. The components 144 may be recycled to the reactor 106 or sent to other users. The downstream system 108 may be configured to remove the relatively small amount of hydrocarbons 146 (e.g., C5+) from the effluent 110 that are heavier than the olefin 102. In all, removal of the components 144 and the hydrocarbons 146 from the effluent 110 may give the olefin 102 product as generally a mixture of ethylene, propylene, and butene. Thus, C2=, C3=, and C4=(including one or more of the four isomers of C4=) can be products. If desired, these products can be separated from each other further downstream. Lastly, in some implementations, the hydrocarbons 146 are not separated (removed) from the effluent 110 but instead are forwarded on in the olefin 102 product. Thus, in those implementations, the olefin 102 product includes a mixture of ethylene, propylene, butene, and a relatively small amount (e.g., less than 5 mol %) of C5+ hydrocarbons.

To separate the components 144 (and hydrocarbons 146 if separated) from the effluent 110, the downstream system 106, e.g., separation system(s), may include membrane separator vessel(s), distillation column(s), stripper column(s) having packing or trays, or vessel(s) having adsorbent (that adsorbs and can be regenerated), or any combinations thereof. Various configurations are applicable. The separation of the components 144 from the effluent 110 in the downstream system 108 may involve multi-stage cooling (including partial condensation). The cooling and partial condensation may utilize heat exchanger(s)), refrigeration compressor(s), and the like. The multi-stage cooling may involve separation, such as via flash separation vessels, and the like.

The system 100 for producing olefin may include a control system 148 that may facilitate or direct operation of the system 100, such as in the operation of equipment and the supply or discharge of flow streams (including flow rate and pressure) and associated control valves. The control system 148 may receive data from sensors (e.g., temperature, pressure, etc.) and online analytical instruments in the system 100. The control system 148 may perform calculations. The control system 148 may specify set points for control devices in the system 100. The control system 148 may be disposed in the field or remotely in a control room. The control system 148 may include control modules and apparatuses distributed in the field.

The control system 148 may include a processor 150 and memory 152 storing code (e.g., logic, instructions, etc.) executed by the processor 150 to perform calculations and direct operations of the system 100. The control system 148 may be or include one or more controllers. The processor 150 (hardware processor) may be one or more processors and each processor may have one or more cores. The hardware processor(s) may include a microprocessor, a central processing unit (CPU), a graphic processing unit (GPU), controller card, circuit board, or other circuitry. The memory 152 may include volatile memory (e.g., cache and random access memory), nonvolatile memory (e.g., hard drive, solid-state drive, and read-only memory), and firmware. The control system 148 may include a desktop computer, laptop computer, computer server, programmable logic controller (PLC), distributed computing system (DSC), controllers, actuators, or control cards.

The control system 148 may receive user input that specifies the set points of control devices or other control components in the system 100. The control system 148 typically includes a user interface for a human to enter set points and other targets or constraints to the control system 148. In some implementations, the control system 148 may calculate or otherwise determine set points of control devices. The control system 148 may be communicatively coupled to a remote computing system that performs calculations and provides direction including values for set points. In operation, the control system 148 may facilitate processes of the system 100 including to direct operation of the reactor 106 and the downstream system 108. Again, the control system 148 may receive user input or computer input that specifies the set points of control components in the system 100. The control system 148 may determine, calculate, and specify the set point of control devices. The determination can be based at least in part on the operating conditions of the system 100 including feedback information from sensors and instrument transmitters, and the like.

Some implementations may include a control room that can be a center of activity, facilitating monitoring and control of the process or facility. The control room may contain a human machine interface (HMI), which is a computer, for example, that runs specialized software to provide a user-interface for the control system. The HMI may vary by vendor and present the user with a graphical version of the remote process. There may be multiple HMI consoles or workstations, with varying degrees of access to data. The control system 148 can be a component of the control system based in the control room. The control system 148 may also or instead employ local control (e.g., distributed controllers, local control panels, etc.) distributed in the system 100. The control system 148 can include a control panel or control module disposed in the field.

Figure 2:
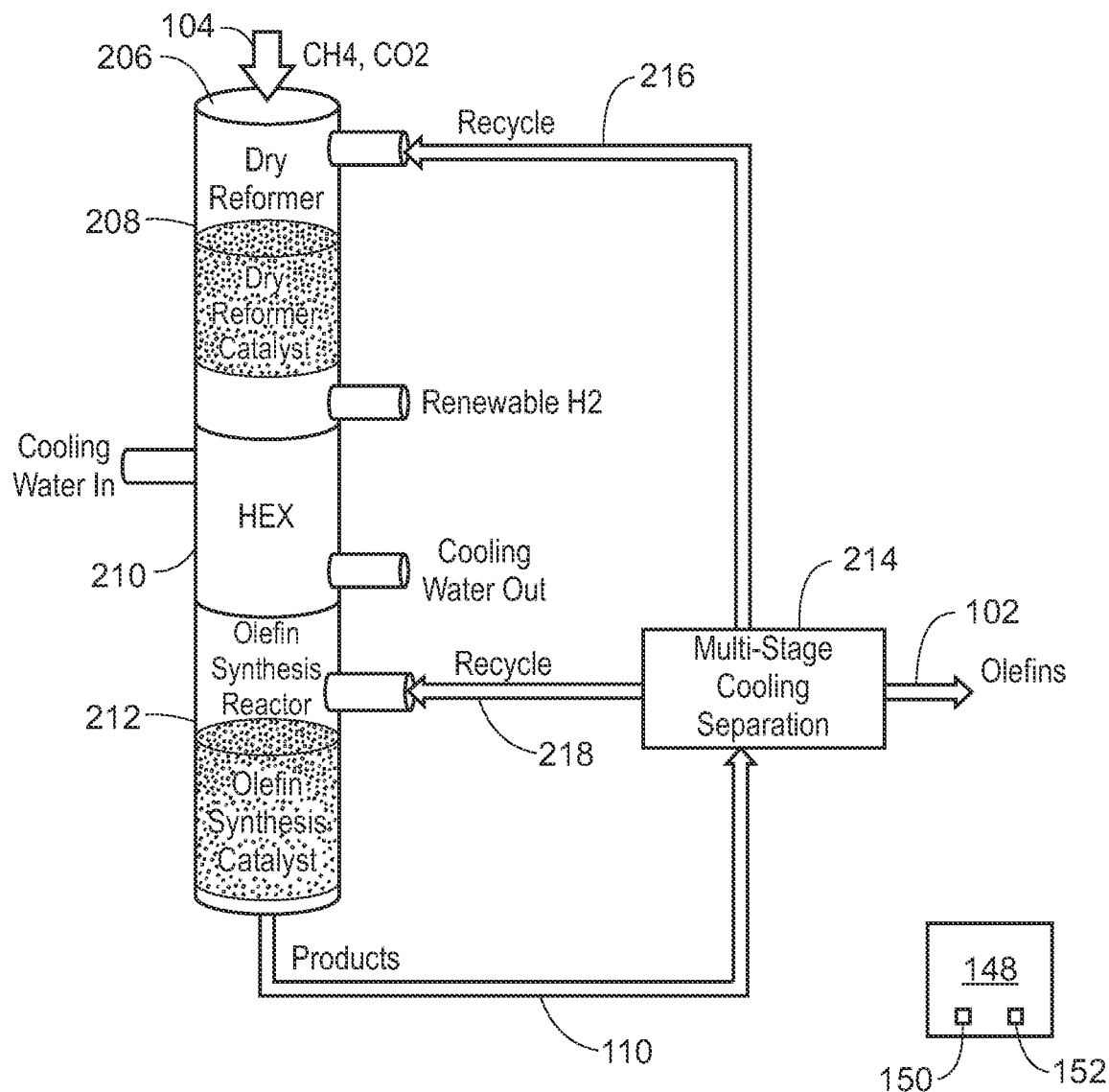
FIG. 2 is a diagram of a system that produces olefin, and which may be analogous to FIG. 1.

FIG. 2 is a system 200 that produces olefin 102 (alkene), such as ethylene, propylene, or butene, or any combinations thereof. In implementations, the olefin 102 may be understood to be olefins 102. In other words, the olefin 102 may be a mixture of light olefins including C2=, C3=, and C4=. The olefins 102 stream can include relatively small amounts of additional hydrocarbon that is not light olefins.

The system 200 includes a reactor 206 that performs dry reforming of $CH_4$. The feed 104 to the reactor 206 includes $CO_2$ and $CH_4$. The dry reforming of $CH_4$ with $CO_2$ as the oxidant is a technique that beneficially converts the greenhouse-gases $CO_2$ and $CH_4$ into syngas that is primarily $H_2$ and CO. The molar ratio $H_2$ to CO in the syngas may deviate from ideal thermodynamic equilibrium of 1 to, for example, in the range of 0.4 to 1. Hydrogen may be added to the syngas in the reactor 206 to increase the molar ratio of $H_2$ to CO if desired.

The reactor 206 may be analogous to the reactor 106 of FIG. 1. The reactor 206 may include two reactors in the same reactor vessel: a reactor for dry reforming $CH_4$ to generate syngas and a reactor for olefin synthesis from the syngas.

The reactor 206 is a vessel having at least three parts or sections (zones): dry reformer 208, heat exchanger 210, and olefin synthesis reactor 212, which are in the same vessel and analogous to the dry reforming section 114, heat exchange section 118, and olefin synthesis section 128 of FIG. 1, respectively. Thus, the dry reformer 208 reactor and the olefin synthesis reactor 212 are in the same reactor vessel. In this implementation, the heat exchanger is also disposed in the same reactor vessel between the dry reformer 208 reactor and the olefin synthesis reactor 212.

The feedstock for the dry reforming may generally include natural gas (primarily $CH_4$) and $CO_2$. The dry reforming may be a technique for conversion of $CO_2$ and $CH_4$ into syngas without the introduction of steam (water). Implementations are performed without introduction of oxygen. Thus, embodiments of the dry reforming are not steam reforming, not mixed-steam $CO_2$ reforming (MSCR) (which may also be known as bi-reforming), and not autothermal reforming (ATR).

The feed 104 to the reactor 206 includes $CO_2$ and $CH_4$. Natural gas may be fed to provide the $CH_4$. Natural gas includes primarily $CH_4$, for example, at 70-90 mol %. Natural gas may include higher alkanes (e.g., ethane, propane, butane) and other components (e.g., nitrogen, hydrogen sulfide, etc.) at a combined concentration, for example, less than 30 mol %. In certain embodiments, the natural gas includes at least 80 mol % $CH_4$ or at least 90 mol % $CH_4$. The natural gas may be combined with a $CO_2$ stream having primarily $CO_2$ to give the feed 104. In embodiments, the natural gas may have no measurable $O_2$ and/or measurable water ($H_2O$), or have trace amounts of $O_2$ and/or $H_2O$. Natural gas generally has no more than 1 mol % of 02 and no more than 1 mol % of $H_2O$. If natural gas is fed, the natural gas and the $CO_2$ of the feed 104 may be fed in a combined stream or as separate streams to the dry reformer 208 of the reactor 206. The flow rate (e.g., volumetric rate, mass rate, or molar rate) of the feed 104 may be controlled via at least one flow control valve (disposed along a supply conduit) or by a mechanical compressor, or a combination thereof. The ratio (e.g., molar, volumetric, or mass ratio) in the feed 104 of the natural gas (or the $CH_4$ in the natural gas) to the $CO_2$ may be adjusted by modulating (e.g., via one or more control valves) at least one of the flow rates of the natural gas or $CO_2$ streams. The supply pressure of the feed 104 may provide for or facilitate the operating pressures in the reactor 106. Moreover, in one implementation, the system 200 may include upstream equipment (e.g., desulfurizer, pre-reformer, etc.) to process or treat the feed 104.

The $CH_4$ content (or natural gas content) in the feed 104 may be at a volume concentration, for example, in the ranges of 20% to 60%, 25% to 60%, or 25% to 50%, or less than 60 vol %, less than 50 vol %, or less than 30 vol %. The $CO_2$ content in the feed 104 may be at a volume concentration in the ranges of 40% to 80%, 40% to 75%, or 50% to 75%, or at least 40 vol %, at least 50 vol %, or at least 75 vol %.

In certain embodiments, the dry reforming in the dry reformer 208 is a fixed-bed catalytic process. Thus, the dry reformer 208 may have a fixed bed of dry reformer catalyst (dry reforming catalyst). The dry reforming in the dry reformer 208 may be a catalytic reaction where, for instance, the catalyst has an oxide support with active metal or metal sites available for the reaction. The dry reformer catalyst may be, for example, a nickel-based catalyst. The dry reformer catalyst may be or include, for example, noble metals, nickel (Ni), or Ni alloys. In some embodiments, the catalyst is magnesium oxide (MgO) or MgO nanoparticles. The MgO or MgO nanoparticles may be promoted with Ni and/or molybdenum (Mo), for example. In one implementation, the catalyst is MgO nanoparticles promoted with Ni and Mo. Other dry reformer catalysts are applicable.

Again, the feed 104 to the reactor 206 and thus to the dry reformer 208 includes $CH_4$ and $CO_2$. While $O_2$ is generally not fed to the dry reformer 208, 02 may be involved in the dry reforming via the dissociation of the $CO_2$. With respect to the dry reforming mechanism, the dry reforming may disassociate $CO_2$ into $O_2$ and CO. A re-oxidation reaction may occur via the $O_2$ at reduced oxide sites of the catalyst support in some implementations. The oxygen from the oxide site of the catalyst support can react with $CH_4$ to produce CO and $H_2$ as contribution to the syngas.

The dry reforming reaction is typically endothermic. Thus, in operation, heat is added to the dry reformer 208. In some implementations, the portion of the reactor 206 vessel having the dry reformer 208 may have a vessel jacket for flow of heat transfer fluid (e.g., steam, hot oil, hot synthetic fluid, etc.) to transfer heat from the heat transfer fluid from the jacket through the vessel wall to the dry reforming reaction mixture in the dry reformer 208. In addition or in lieu of a vessel jacket, electrical heaters may provide heat for the endothermic dry reforming reaction. The electrical heaters may be disposed in the reactor 206 vessel in the dry reformer 208 or on an external surface of reactor 206 vessel at the dry reformer 208. Other configurations of heat transfer and temperature control of the dry reformer 208 are applicable. The operating temperature in the dry reformer 208 may be, for example, at less than 850° C., less than 800° C., in the range of 700° C. to 900° C., in the range of 750° C. to 875° C., or in the range of 800° C. to 850° C. The operating pressure in the dry reformer may be, for example, in the range of 1 bar to 50 bars.

As discussed, hydrogen may be added to the reactor 206 to increase the molar ratio of $H_2$ to CO of the syngas generated by the dry reformer 208. Hydrogen may be added to the reactor 206 vessel at a discharge portion of the dry reformer 208 or at other parts of the reactor 206. The source of the $H_2$ may be, for example, a $H_2$ piping header or a $H_2$ tube trailer, and the like. In some implementations, the source of the $H_2$ is a water electrolysis unit. The $H_2$ supplied by the water electrolysis unit may be labeled as renewable $H_2$ in implementations in which the water electrolysis unit is driven by renewable energy sources, such as energy sources relying on wind or solar.

The syngas (including any added $H_2$) is cooled in the heat exchanger 210. The heat exchanger 210 is generally disposed within the reactor 206 vessel. In operation, the heat exchanger 210 cools (removes heat from) the syngas discharged from the dry reformer 208 The cooling medium for the heat exchanger 210 may be, for example, cooling water. The cooling medium may flow through the heat exchanger 210 to absorb heat from the syngas. The heat exchanger 210 may be, for example, a shell-and-tube heat-exchanger type or configuration in which the tubes are situated in the reactor 206 vessel. The reactor 206 vessel wall may act as the shell of the heat exchanger 210 housing the tubes, or the shell of the heat exchanger 210 housing the tubes is disposed in the reactor 206 vessel. Other heat exchanger configurations are applicable.

The olefin synthesis reactor 212 in the reactor 206 vessel receives the cooled syngas discharged from the heat exchanger 210. The olefin synthesis reaction in the olefin synthesis reactor 212 that converts the syngas to olefin 102 is generally exothermic. Therefore, the reactor 206 vessel at the olefin synthesis reactor 212 may have a vessel jacket for a heat-transfer fluid that is a cooling medium (e.g., cooling water). In addition to (or in lieu of) a vessel jacket, the reactor 206 vessel may have cooling coils internally in the olefin synthesis reactor 212 that route a cooling medium. The operating temperature in the olefin synthesis reactor 212 may be, for example in a range of 250° C. to 450° C., or in a range of 290° C. to 410° C. The operating pressure may be, for example, in a range of 10 bars to 50 bars.

The olefin synthesis reactor 212 has olefin synthesis catalyst to convert the syngas to olefin (e.g., olefin 102). The olefin synthesis catalyst may be, for example, a zinc chromium oxide (ZnCrOx)-based catalyst, mixed oxide-zeolite catalysts, a bi-functional catalyst including a (ZnCrOx)-based catalyst and a zeolite catalyst, hybrid catalysts composed of Zn-M catalysts (M=$Al_2O_3$, $ZrO_2$, $Cr_2O_3$, and $CeO_2$) and zeolite (e.g., SAPO-34 zeolite), CrZn—SAPO-34 catalyst, bifunctional catalyst consisting of Mn—Ga oxide and SAPO-34, iron-based catalysts, and modified iron catalysts. As one example, a bifunctional catalyst (chromium oxide/zinc oxide-SAPO-34) for converting syngas to olefins is disclosed in US Patent Application Publication No. 2018/0305272A1, which is incorporated herein by reference in its entirety. Other catalysts are applicable.

The olefin 102 generated via the olefin synthesis may be lower or lighter olefins (4 carbons or less), such as C2=, C3=, or C4=, or any combinations thereof. The C4= may include one or more of the four isomers of C4=. This olefin 102 (e.g., a mixture of C2=, C3=, and C4=) may discharge in the reactor 206 effluent 110 from the olefin synthesis reactor 212 and thus from the reactor 206 vessel in the illustrated implementation.

The system 200 may include a separation system 214 that may be analogous to the downstream system 108 of FIG. 1. In FIG. 2, the effluent 110 may be processed in the separation system 214 to give the olefins 102 product. Components (e.g., $H_2$, CO, $CO_2$, $CH_4$, etc.) may be removed from the effluent 104 to give the product olefins 102. These removed components may be recycled to the reactor 206. In the illustrated embodiment, two recycle streams 216, 218 having at least some of these removed components are depicted. The recycle stream 216 is fed to the dry reformer 208. The recycle stream 218 is fed to the olefin synthesis reactor 212. In implementations, the recycle streams 216, 218 may each be primarily (e.g., at least 50 mol %) of the combination of $H_2$ and CO. The recycle stream 216 and the recycle stream 218 may have the same composition. On the other hand, the recycle stream 216 may have a composition different than the composition of the recycle stream 218. For instance, the concentration of $CO_2$ in the recycle stream 216 may be greater than the concentration of $CO_2$ than the recycle stream 218.

The separation system 214 may employ, for example, a multi-stage cooling separation. The separation system 214 may be or include a multi-stage cooling separation unit. The multi-stage cooling may include condensation and flash separation. The gas phase flow of a flash separation vessel after cooling and partial condensation may enter the next flash separation vessel. The separation system(s) may include a membrane separator vessel, a distillation column, a vessel having adsorbent, and so forth. The product olefins 102 stream discharged from separation system 214 (e.g., multi-stage cooling separation system) can include a mixture C2=, C3=, and C4=, as well other hydrocarbons.

The system 200 may include the control system 148, as discussed with respect to FIG. 1. The control system 146 may direct or facilitate operations of the system 200.

Figure 3:
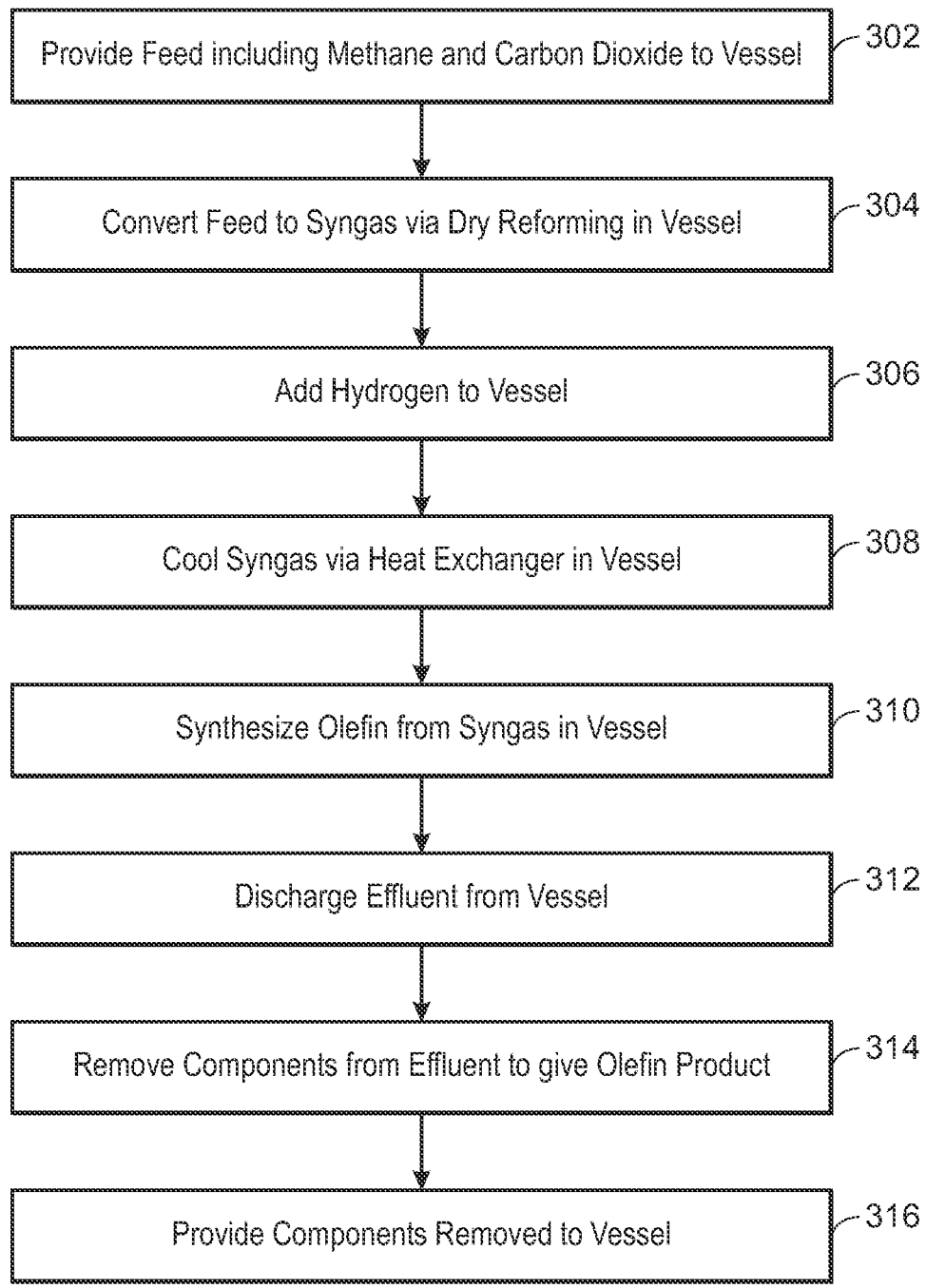
FIG. 3 is a block flow diagram of a method of producing olefin via dry reforming and olefin synthesis in the same vessel

FIG. 3 is a method 300 of producing olefin via dry reforming and olefin synthesis in the same vessel. The vessel may be a reactor vessel. The vessel may be a vessel of a reactor.

Thus, a reactor having a reactor vessel may perform both the dry reforming and olefin synthesis in the same reactor vessel. Therefore, the reactor may perform two different types of reaction (dry reforming and olefin synthesis) in the same reactor vessel.

At block 302, the method includes providing feed including methane and carbon dioxide to the vessel. The method may provide the feed to a dry reformer (or dry reforming section) in the vessel. Again, the vessel may be a vessel of a reactor and thus be labeled as the reactor vessel. The vessel may have a feed inlet (e.g., inlet nozzle) to receive the feed. The feed inlet nozzle may be coupled (e.g., flanged connection, threaded connection, etc.) to a supply conduit conveying the feed to the vessel. The vessel may include more than one feed inlet nozzles to receive the feed. In certain implementations, a control valve is disposed along a conduit conveying the carbon dioxide for the feed. The control valve controls flow rate of the carbon dioxide to give a specified amount of carbon dioxide of the feed. Thus, the method may include controlling the flow rate of the carbon dioxide provided for the feed to the vessel to give a specified amount of carbon dioxide of the feed. The specified amount of carbon dioxide of the feed may be, for example, ratio (e.g., molar ratio) of the carbon dioxide to the methane of the feed or a concentration (e.g., vol % or mol %) of the carbon dioxide in the feed.

At block 304, the method includes converting the methane and the carbon dioxide by dry reforming (e.g., via dry reforming catalyst) in the vessel into syngas including hydrogen and carbon monoxide. The dry reforming may be performed via the dry reforming catalyst in a dry reformer (or dry reforming section) in the vessel. The dry reforming catalyst may be a fixed bed of catalyst in the dry reforming section (dry reformer) in the vessel.

At block 306, the method may include adding hydrogen to the vessel, such as to increase the ratio (e.g., molar ratio) in the syngas of hydrogen to carbon monoxide. The vessel may have a hydrogen inlet (e.g., inlet nozzle) coupled to a hydrogen supply conduit (external to the vessel) to receive the hydrogen to increase the molar ratio of hydrogen to carbon monoxide of the syngas in the vessel. In some implementations, a water electrolysis unit (including a water-electrolysis electrochemical cell) provides the hydrogen through the hydrogen supply conduit to the hydrogen inlet on the vessel. In certain implementations, a flow control valve is disposed along the supply conduit conveying the hydrogen to the hydrogen inlet on the vessel, wherein the control valve controls flow rate of the hydrogen from the hydrogen source (e.g., water electrolysis unit) to the vessel.

At block 308, the method includes cooling the syngas via a heat exchanger (heat exchange section) in the vessel. The method may include flowing the syngas from the dry reforming section through the heat exchange section in the vessel to cool the syngas with a cooling medium (e.g., cooling water) in the heat exchange section. The heat exchange section may include the heat exchanger that cools the syngas with the cooling medium, and wherein flowing the syngas from the dry reforming section through the heat exchange section includes flowing the syngas through the heat exchanger (e.g., shell-and-tube heat exchanger).

At block 310, the method includes synthesizing olefin (e.g., via olefin synthesis catalyst) from the syngas in the vessel. The method may include flowing the syngas as cooled from the heat exchange section (heat exchanger) to the olefin synthesis section in the vessel, and synthesizing olefin from the syngas via the olefin synthesis catalyst in the olefin synthesis section. The olefin synthesis catalyst may be a fixed bed of catalyst in the olefin synthesis section (olefin synthesis reactor) in the vessel. The olefin synthesized includes ethylene, propylene, or butene, or any combinations thereof. In implementations, the olefin is a mixture of ethylene, propylene, and butene.

At block 312, the method includes discharging effluent (having the olefin) from the vessel. The vessel may have an outlet discharge nozzle to discharge the effluent from the vessel into an effluent discharge conduit. The discharging of the effluent from the vessel may be discharging the effluent from the olefin synthesis section (or olefin synthesis reactor) in the vessel. Again, the vessel may have an effluent outlet (outlet nozzle) coupled to an effluent discharge conduit external to the vessel for discharge of the effluent from the vessel (e.g., to a separation system, as discussed with respect to block 314).

At block 314, the method may include processing the effluent (as discharged) to remove components (e.g., hydrogen, carbon monoxide, carbon dioxide, C5+ hydrocarbons, any unreacted methane, etc.) from the effluent to give the olefin as product. In implementations, the combination of hydrogen and carbon dioxide may the majority (e.g., greater than 50 mol %) of the components removed. The third most prevalent component (after hydrogen and carbon dioxide) removed may be, for example, carbon dioxide. In other words, in those implementations, the three most prevalent components (greatest mol %) of the components removed is hydrogen, carbon monoxide, and carbon dioxide. The processing of the effluent to remove the components may be performed in a separation system (e.g., including at least one flash vessel). In implementations, the separation system may be a multi-stage cooling (including partial condensation) system. Other unit operations for the separation system may be implemented, such as membrane separation (membrane separator vessel), distillation (distillation column), and so on.

At block 316, the method may include providing (recycling, returning) at least one of the components removed from the effluent to the vessel. The vessel may include an inlet (e.g., an inlet nozzle) to receive at least one of the components removed from the effluent. The inlet nozzle may be coupled to a conduit conveying the component(s) from the separation system. The method may include providing (e.g., via a conduit) at least one of the hydrogen, the carbon monoxide, or the carbon dioxide removed from the effluent to the dry reforming section (dry reformer) in the vessel. The vessel may have an inlet nozzle at the dry reforming section to receive this return of component(s) to the vessel. The method may include providing (e.g., via a conduit) at least one of the hydrogen, the carbon monoxide, or the carbon dioxide removed from the effluent to the olefin synthesis section. The vessel have an inlet nozzle at the olefin synthesis section to receive this return of component(s) to the vessel.

The present techniques uniquely recognize the feasibility and benefits of combining dry reforming with olefin synthesis (in the same vessel), as describe herein.

An embodiment is a method of producing olefin via dry reforming and olefin synthesis, the method including providing feed including methane and carbon dioxide to a vessel, converting methane and carbon dioxide in the vessel into syngas (that includes hydrogen and carbon monoxide) via dry reforming in the vessel, and cooling the syngas via a heat exchanger in the vessel. The method includes synthesizing olefin from the syngas in the vessel, wherein the olefin includes ethylene, propylene, or butene, or any combinations thereof. The method includes discharging the effluent from the vessel, the effluent including the olefin. The olefin may be a mixture of ethylene, propylene, and butene. The method may include processing the effluent as discharged to remove components from the effluent to give the olefin as product, the components including hydrogen, carbon monoxide, and carbon dioxide. If so, the method may include recycling the hydrogen, the carbon monoxide, and the carbon dioxide removed from the effluent to the vessel. The converting of the methane and the carbon dioxide in the vessel may involve converting the methane and the carbon dioxide via dry reforming catalyst in the vessel into the syngas, and wherein synthesizing the olefin may involve synthesizing the olefin from the syngas via olefin synthesis catalyst in the vessel. The method may include adding hydrogen to the vessel to increase a molar ratio of hydrogen to carbon monoxide of the syngas.

Another embodiment is a method of producing olefin, including converting (involving dry reforming) methane and carbon dioxide via a dry reforming catalyst in a dry reforming section in a reactor vessel into syngas that includes hydrogen and carbon monoxide. The method may include providing feed including the methane and the carbon dioxide to the dry reforming section in the reactor vessel. The method includes flowing the syngas from the dry reforming section through a heat exchange section in the reactor vessel to cool the syngas with a cooling medium in the heat exchange section. The heat exchange section may include a heat exchanger that cools the syngas with the cooling medium, and wherein flowing the syngas from the dry reforming section through the heat exchange section includes flowing the syngas through the heat exchanger. The method includes flowing the syngas as cooled from the heat exchange section to an olefin synthesis section in the reactor vessel. The method includes synthesizing olefin from the syngas via an olefin synthesis catalyst in the olefin synthesis section, wherein the olefin includes ethylene, propylene, or butene, or any combinations thereof. The method may include discharging effluent having the olefin from the reactor vessel. The method may include processing effluent including the olefin discharged from the reactor vessel to remove hydrogen, carbon monoxide, and carbon dioxide from the effluent to give the olefin as product. If so, the method may include providing at least one of the hydrogen, the carbon monoxide, or the carbon dioxide removed from the effluent to the dry reforming section. The method may include providing at least one of the hydrogen, the carbon monoxide, or the carbon dioxide removed from the effluent to the olefin synthesis section.

Yet another embodiment is an olefin production system including a reactor vessel having a feed inlet to receive a feed including methane and carbon dioxide. A control valve may be disposed along a conduit conveying the carbon dioxide for the feed to control flow rate of the carbon dioxide to give a specified amount of carbon dioxide of the feed. If so, the specified amount can be a ratio of the carbon dioxide to the methane of the feed or a concentration of the carbon dioxide in the feed. The reactor vessel has a dry reforming section (having a dry reforming catalyst) in the reactor vessel to convert the methane and the carbon dioxide into syngas that includes hydrogen and carbon monoxide. The reactor vessel has a heat exchange section (having a heat exchanger) in the reactor vessel to receive the syngas from the dry reforming section and cool the syngas with a cooling medium. In implementations, the heat exchanger is a shell-and-tube heat exchanger, and wherein the cooling medium is cooling water. The reactor vessel includes an olefin synthesis section (having an olefin synthesis catalyst) in the reactor vessel to synthesize olefin from the syngas and discharge an effluent including the olefin from the reactor vessel, wherein the olefin comprises ethylene, propylene, butene, or any combinations thereof. The olefin production system may include a separation system to remove components from the effluent as discharged to give the olefin as olefin product, the components removed including hydrogen, carbon monoxide, and carbon dioxide, wherein the separation system includes a flash vessel, and wherein the reactor vessel has an effluent outlet for discharge of the effluent from the reactor vessel. In implementations, the reactor vessel has an inlet to receive at least one of the components removed from the effluent. The dry reforming catalyst may be a fixed bed of catalyst in the dry reforming section in the reactor vessel. The olefin synthesis catalyst may be a fixed bed of catalyst in the olefin synthesis section in the reactor vessel. The reactor vessel may have a hydrogen inlet to receive hydrogen to increase a molar ratio of hydrogen to carbon monoxide of the syngas in the reactor vessel. If so, the olefin production system may include a water electrolysis unit having a water-electrolysis electrochemical cell to provide the hydrogen to the hydrogen inlet of the reactor vessel. A control valve may be disposed along a conduit conveying the hydrogen to the hydrogen inlet of the reactor vessel, wherein the control valve controls flow rate of the hydrogen from the water electrolysis unit to the reactor vessel.

EXAMPLES

The Examples are given only as examples and not meant to limit the present techniques. Examples 1-4 are presented.

Examples 1 and 2

Conditions of Examples 1 and 2 are given in Table 1. In Example 1, the feed (excluding nitrogen) was 50 mol % $CO_2$ and 50 mol % $CH_4$. In Example 2, the feed (excluding nitrogen) was 75 mol % $CO_2$ and 25 mol % $CH_4$. Nitrogen gas was fed along with the $CH_4$ and $CO_2$. Nitrogen is inert and does not react.

In Example 1, an evaluation of a dry reforming catalyst was performed in the laboratory with micro-reactor and online gas chromatography (GC). The micro-reactor was a stainless-steel tube with diameter of 9 millimeters (mm) mounted in a furnace. During the micro-scale testing, about 1 gram of catalyst was added to the tube, and the tube mounted in the furnace. Methane, carbon dioxide, and nitrogen were introduced into the tube in the furnace by a mass flow controller. The temperature of reactor was increased up to 800° C. with a ramp of 10° C./minute and kept at 800° C. during the reaction. Composition of effluent gas discharged from the reactor (from the tube) was analyzed from online GC in order to calculate conversions and $H_2/CO$ molar ratio. The time on stream for the reaction was 850 hours. The conversion of $CH_4$ and the conversion of $CO_2$ were both about 100% over the entire 850 hours.

In Example 2, an evaluation of the dry reforming catalyst (same catalyst as in Example 1) was performed in the laboratory with micro-reactor and online gas chromatography (GC). The micro-reactor was a stainless-steel tube with diameter of 9 millimeters (mm) mounted in a furnace. During the micro-scale testing, about 1 gram of catalyst was added to the tube, and the tube mounted in the furnace. Methane, carbon dioxide, and nitrogen were introduced to the furnace by a mass flow controller. The temperature of reactor was increased up to 800° C. with a ramp of 10° C./minute and kept at 800° C. during the reaction. Composition of effluent gas discharged from the reactor was analyzed from online GC in order to calculate conversions and $H_2/CO$ molar ratio. The time on stream for the reaction was 24 hours. The conversion of $CH_4$ over the 24 hours was consistently about 95%. The conversion of $CO_2$ over the 24 hours was consistently about 45%.

TABLE 1

Evaluation of dry reforming catalyst-Example 1 and Example 2

|  | Example 1 | Example 2 |
| --- | --- | --- |
| Catalyst | Nickel-based catalyst | Nickel-based catalyst |
| CO2 Feed | 50% | 75% |
| CH4 Feed | 50% | 25% |
| Temperature | 800° C. | 800° C. |
| Pressure | 1 bar | 14 bars |
| Conversions | CH4:100%, CO2:100% | CH4: ~95%, SO2: ~45% |
| H2/CO molar ratio | ~1 | ~0.5 |
| Time on stream (hours) | 850 | 24 |

Examples 3 and 4

A reactor was simulated via Aspen Plus® software (version 10). Aspen Plus® software is available from Aspen Technology, Inc. having headquarters in Bedford, Mass., USA. The reactor simulated has a dry reforming part and olefin synthesis part (and heat exchanger disposed there between), such as the reactor 106, 206 discussed above with respect to FIGS. 1-2.

Figure 4:
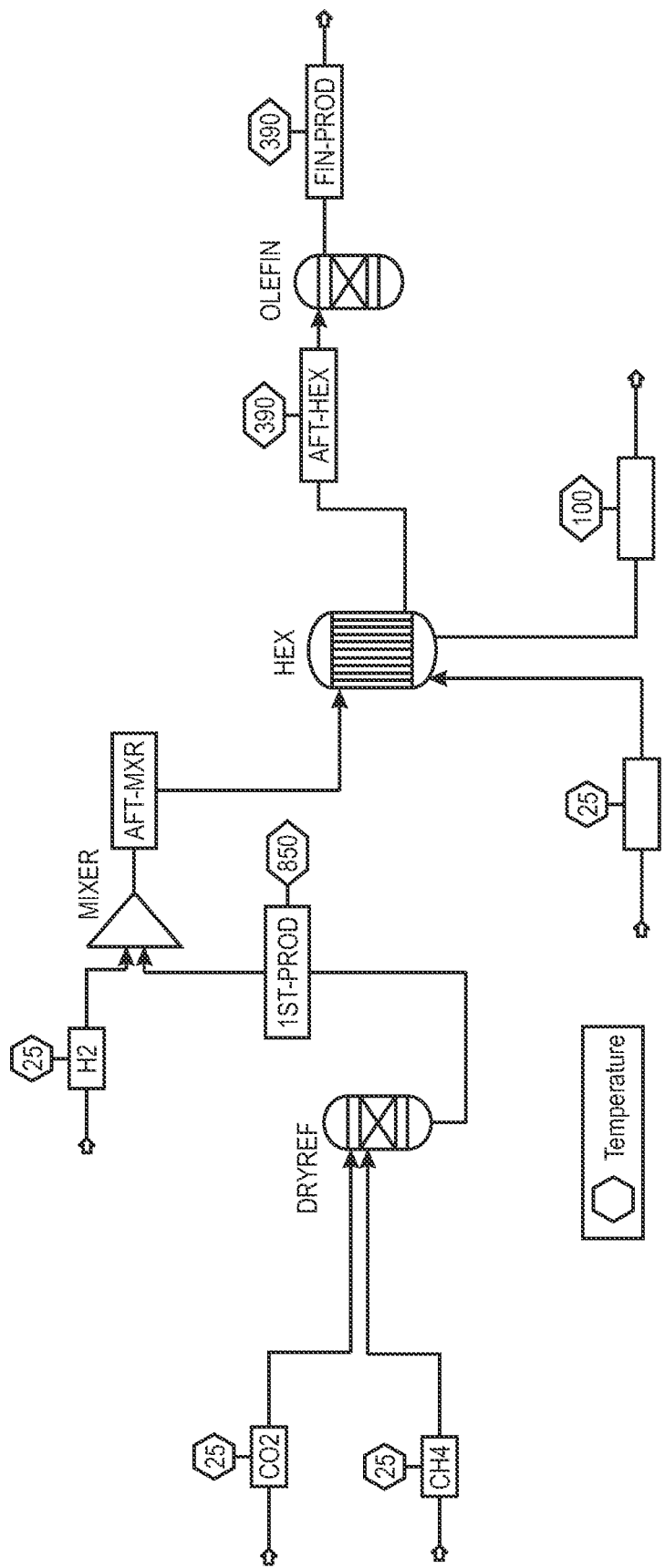
FIG. 4 is an Aspen Plus® simulation diagram.

FIG. 4 is the Aspen simulation diagram for the two simulations performed in Example 3 and Example 4, respectively. The stream temperatures depicted in FIG. 4 is in ° C. The stream information for the stream labels in FIG. 4 is in Table 4 (Example 3) and Table 7 (Example 4) below. In the simulations, the Aspen stoichiometric reactor was utilized for simulating the dry reforming part and the olefin synthesis part, respectively. The Aspen heat exchanger was applied to mimic the heat exchanger part. For dry reforming conditions and conversions, the aforementioned catalyst experimental results (as seen in Table 1) were applied. Olefin synthesis conditions are typical conditions. The values for olefins selectivity and CO conversion input are related to the ZnCrOx based catalyst.

Based on the simulation results for Example 3, it was found that 31.6 kilogram per day (kg/day) of $CO_2$, 11.55 kg/day of $CH_4$ and 2.9 kg/day of extra $H_2$ enabled to ideally produce 2.28 kg/day of olefin. Based on the simulation results for Example 4, 11.55 kg/day of $CH_4$, 95.06 kg/day of $CO_2$ and 5.81 kg/day of extra $H_2$ can ideally produce 3.04 kg/day of olefin. In the simulation results, the HC-OTHER in Table 7 is ethane, butane, etc.

TABLE 2

Dry Reforming Conditions for Example 3

Dry reforming condition 1

| Feed | 50 mol % CH4, 50 mol % CO2 |
| --- | --- |
| Catalyst | Ni-based catalyst |
| Temperature | 850° C. |
| Pressure | 40 bars |
| Conversion | 100% CH4, 100% CO2 |
| Products | H2:CO = 1:1 |

TABLE 3

Olefin Synthesis Conditions for Example 3

| Olefin synthesis condition | |
|---|---|
| Feed | H2:CO = 2:1 molar ratio |
| Catalyst | ZnCrOx based catalyst |
| Temperature | 390° C. |
| Pressure | 40 bars |
| Conversion | 25.2% CO |
| Products | 45% C2—C4 Olefins selectivity |

TABLE 4

Stream Information for Example 3

| Stream | CH4 | CO2 | 1ST-PROD | H2 | AFT-MXR | AFT-HEX | FIN-PROD |
|---|---|---|---|---|---|---|---|
| Phase | Vapor | Vapor | Vapor | Vapor | Vapor | Vapor | Vapor |
| Temp (C) | 25 | 25 | 850 | 25 | 588.83 | 390 | 390 |
| Pressure (bar) | 40 | 40 | 40 | 40 | 40 | 40 | 40 |
| Mole Fractions (mol %) | | | | | | | |
| CH4 | 100.0% | 0.0% | 0.0% | 0.0% | 0.0% | 0.0% | 0.1% |
| CO2 | 0.0% | 100.0% | 0.0% | 0.0% | 0.0% | 0.0% | 4.4% |
| H2O | 0.0% | 0.0% | 0.0% | 0.0% | 0.0% | 0.0% | 0.2% |
| H2 | 0.0% | 0.0% | 50.0% | 100.0% | 66.7% | 66.7% | 66.4% |
| CO | 0.0% | 0.0% | 50.0% | 0.0% | 33.3% | 33.3% | 26.7% |
| C2=C4 | 0.0% | 0.0% | 0.0% | 0.0% | 0.0% | 0.0% | 2.0% |
| HC-OTHER | 0.0% | 0.0% | 0.0% | 0.0% | 0.0% | 0.0% | 0.1% |
| HC—C5+ | 0.0% | 0.0% | 0.0% | 0.0% | 0.0% | 0.0% | 0.1% |
| Mass Flows (kg/day) | | | | | | | |
| CH4 | 11.55 | 0.00 | 0.00 | 0.00 | 0.00 | 0.00 | 0.04 |
| CO2 | 0.00 | 31.69 | 0.00 | 0.00 | 0.00 | 0.00 | 7.79 |
| H2O | 0.00 | 0.00 | 0.00 | 0.00 | 0.00 | 0.00 | 0.18 |
| H2 | 0.00 | 0.00 | 2.90 | 2.90 | 5.81 | 5.81 | 5.39 |
| CO | 0.00 | 0.00 | 40.33 | 0.00 | 40.33 | 40.33 | 30.14 |
| C2=C4 | 0.00 | 0.00 | 0.00 | 0.00 | 0.00 | 0.00 | 2.28 |
| HC-OTHER | 0.00 | 0.00 | 0.00 | 0.00 | 0.00 | 0.00 | 0.08 |
| HC—C5+ | 0.00 | 0.00 | 0.00 | 0.00 | 0.00 | 0.00 | 0.24 |

TABLE 5

Dry Reforming Conditions for Example 4

| Dry reforming condition 2 | |
|---|---|
| Feed | 25 mol % CH4, 75 mol % CO2 |
| Catalyst | Ni based catalyst |
| Temperature | 850° C. |
| Pressure | 40 bars |
| Conversion | 100% CH4, 55% CO2 |
| Products | H2:CO = 1:2 molar ratio |

TABLE 6

Olefin Synthesis Conditions for Example 3

| Olefin synthesis condition | |
|---|---|
| Feed | H2:C2:1 molar ratio |
| Catalyst | ZnCrOx based catalyst |
| Temperature | 390° C. |
| Pressure | 40 bars |
| Conversion | 25.2% CO |
| Products | 45% C2—C4 Olefins selectivity |

TABLE 7

Stream Information for Example 4

| Stream | CH4 | CO2 | 1ST-PROD | H2 | AFT-MXR | AFT-HEX | FIN-PROD |
|---|---|---|---|---|---|---|---|
| Temp (C) | 25 | 25 | 850 | 25 | 569.48 | 390 | 390 |
| Pressure (bar) | 40 | 40 | 40 | 40 | 40 | 40 | 40 |
| Mole Fractions (mol %) | | | | | | | |
| CH4 | 100% | 0% | 0% | 0% | 0% | 0% | 0% |
| CO2 | 0% | 100% | 22% | 0% | 13% | 13% | 18% |
| H2O | 0% | 0% | 11% | 0% | 7% | 7% | 7% |
| H2 | 0% | 0% | 22% | 100% | 53% | 53% | 52% |
| CO | 0% | 0% | 44% | 0% | 27% | 27% | 21% |

TABLE 7-continued

Stream Information for Example 4

| Stream<br>Temp (C)<br>Pressure<br>(bar) | CH4<br>25<br>40 | CO2<br>25<br>40 | 1ST-<br>PROD<br>850<br>40 | H2<br>25<br>40 | AFT-<br>MXR<br>569.48<br>40 | AFT-<br>HEX<br>390<br>40 | FIN-PROD<br>390<br>40 |
|---|---|---|---|---|---|---|---|
| C2=C4 | 0% | 0% | 0% | 0% | 0% | 0% | 2% |
| HC-OTHER | 0% | 0% | 0% | 0% | 0% | 0% | 0% |
| HC—C5+ | 0% | 0% | 0% | 0% | 0% | 0% | 0% |
| Mass Flows (kg/day) | | | | | | | |
| CH4 | 11.55 | 0.00 | 0.00 | 0.00 | 0.00 | 0.00 | 0.056 |
| CO2 | 0.00 | 95.06 | 42.25 | 0.00 | 42.25 | 42.25 | 52.64 |
| H2O | 0.00 | 0.00 | 8.65 | 0.00 | 8.65 | 8.65 | 8.89 |
| H2 | 0.00 | 0.00 | 1.94 | 5.81 | 7.74 | 7.74 | 7.19 |
| CO | 0.00 | 0.00 | 53.78 | 0.00 | 53.78 | 53.78 | 40.18 |
| C2=C4 | 0.00 | 0.00 | 0.00 | 0.00 | 0.00 | 0.00 | 3.04 |
| HC-OTHER | 0.00 | 0.00 | 0.00 | 0.00 | 0.00 | 0.00 | 0.11 |
| HC—C5+ | 0.00 | 0.00 | 0.00 | 0.00 | 0.00 | 0.00 | 0.32 |

A number of implementations have been described. Nevertheless, it will be understood that various modifications may be made without departing from the spirit and scope of the disclosure.

What is claimed is:

1. A method of producing olefin via dry reforming and olefin synthesis, the method comprising:
   providing feed comprising methane and carbon dioxide to a dry reforming section in a vessel;
   converting methane and carbon dioxide in the vessel into syngas comprising hydrogen ($H_2$) and carbon monoxide by dry reforming via dry reforming catalyst in the dry reforming section in the vessel;
   flowing the syngas from the dry reforming section to a heat exchanger in the vessel and cooling the syngas via the heat exchanger;
   flowing the syngas from the heat exchanger to a olefin synthesis section in the vessel and synthesizing olefin from the syngas via olefin synthesis catalyst in the olefin synthesis section in the vessel, wherein the olefin comprises ethylene, propylene, or butene, or any combinations thereof;
   injecting $H_2$ into the vessel into the syngas flowing from the dry reforming section to the heat exchanger or into the syngas in the heat exchanger, or a combination thereof, to increase a molar ratio of $H_2$ to carbon monoxide of the syngas;
   controlling flow rate of the $H_2$ injected via a control valve disposed along a conduit conveying the $H_2$ for injection into the vessel; and
   discharging effluent from the vessel, the effluent comprising the olefin.

2. The method of claim 1, comprising heating the dry reforming section in the vessel and cooling the methanol synthesis section in the vessel, wherein oxygen ($O_2$) is not introduced into the vessel for the dry reforming, wherein the $H_2$ injected to increase the molar ratio of $H_2$ to carbon monoxide in the syngas is not injected into olefin synthesis section, and wherein the olefin comprises a mixture of ethylene, propylene, and butene.

3. The method of claim 1, comprising:
   processing the effluent as discharged to remove components from the effluent to give the olefin as product, the components comprising hydrogen, carbon monoxide, and carbon dioxide, wherein the effluent comprises less than 5 mole percent of $C_{5+}$ hydrocarbons; and
   recycling at least one of the hydrogen, the carbon monoxide, or the carbon dioxide removed from the effluent to the dry reforming section in the vessel or to the olefin synthesis section in the vessel, or both, wherein the dry reforming section and the methanol synthesis section are enclosed within the vessel in an interior of the vessel to inside of a vessel wall of the vessel, and wherein the heat exchanger in the vessel is disposed between the dry reforming section and the methanol synthesis section.

4. The method of claim 3, wherein the $H_2$ injected into the syngas comprises $H_2$ generated via a water electrolysis unit comprising a water-electrolysis electrochemical cell, wherein the conduit conveying the $H_2$ for injection to the vessel is coupled to the water electrolysis unit to receive $H_2$ as generated by the water electrolysis unit.

5. The method of claim 1, comprising measuring composition of the effluent and in response to the composition as measured, adjusting at least one of flow rate of the carbon dioxide stream or flow rate of the $H_2$ injected into the syngas in the vessel, wherein the vessel comprises metal divider plates as vessel internals for division into the dry reforming section, the heat exchanger as a section, and the methanol synthesis section.

6. The method of claim 1, wherein providing the feed comprises:
   combining a carbon dioxide stream having at least 90 mole percent (mol %) of carbon dioxide with a methane stream having at least 70 mol % of methane to give the feed; and
   controlling flow rate of the carbon dioxide stream via a control valve disposed along a conduit conveying the carbon dioxide stream.

7. A method of producing olefin, comprising:
   converting methane and carbon dioxide via a dry reforming catalyst in a dry reforming section in a reactor vessel into syngas comprising hydrogen ($H_2$) and carbon monoxide, wherein the converting comprises dry reforming via dry reforming catalyst in the dry reforming section;
   flowing the syngas from the dry reforming section through a heat exchange section in the reactor vessel to cool the syngas with a cooling medium in the heat exchange section;

flowing the syngas as cooled from the heat exchange section to an olefin synthesis section in the reactor vessel;

synthesizing olefin from the syngas via an olefin synthesis catalyst in the olefin synthesis section, wherein the olefin comprises ethylene, propylene, or butene, or any combinations thereof, wherein the dry reforming section and the methanol synthesis section are enclosed within the reactor vessel in an interior of the reactor vessel to inside of a vessel wall of the reactor vessel, and wherein the heat exchange section in the reactor vessel is disposed between the dry reforming section and the methanol synthesis section;

injecting $H_2$ into the syngas in the reactor vessel to increase a molar ratio of $H_2$ to carbon monoxide of the syngas, wherein the $H_2$ injected is injected into the syngas flowing from the dry reforming section to the heat exchanger or injected into the syngas in the heat exchanger, or a combination thereof; and controlling flow rate of the $H_2$ injected via a control valve disposed along a conduit conveying the $H_2$ for injection into the reactor vessel.

8. The method of claim 7, comprising:

providing feed comprising the methane and the carbon dioxide to the dry reforming section in the reactor vessel, wherein oxygen ($O_2$) is not introduced into the reactor vessel for the dry reforming, wherein providing the feed comprises:

combining a carbon dioxide stream having at least 90 mole percent (mol %) of carbon dioxide with a methane stream having at least 70 mol % of methane to give the feed; and controlling flow rate of the carbon dioxide stream via a control valve disposed along a conduit conveying the carbon dioxide stream; and discharging effluent comprising the olefin from the reactor vessel, wherein the effluent comprises less than 5 mole percent of $C_{5+}$ hydrocarbons, wherein the dry reforming catalyst is a fixed bed of catalyst in the dry reforming section in the reactor vessel, and wherein the olefin synthesis catalyst is a fixed bed of catalyst in the olefin synthesis section in the reactor vessel.

9. The method of claim 8, comprising measuring composition of the effluent and in response to the composition as measured, adjusting at least one of flow rate of the carbon dioxide stream or flow rate of the $H_2$ injected into the syngas, wherein the heat exchange section comprises a shell-and-tube heat exchanger that cools the syngas with the cooling medium comprising cooling water, and wherein flowing the syngas from the dry reforming section through the heat exchange section comprises flowing the syngas through the shell-and-tube heat exchanger.

10. The method of claim 7, comprising processing effluent comprising the olefin discharged from the reactor vessel to remove hydrogen, carbon monoxide, and carbon dioxide from the effluent to give the olefin as product, wherein the $H_2$ injected to increase the molar ratio of $H_2$ to carbon monoxide in the syngas is not injected into the olefin synthesis section.

11. The method of claim 10, comprising providing at least one of the hydrogen, the carbon monoxide, or the carbon dioxide removed from the effluent to the dry reforming section, wherein the $H_2$ injected into the syngas comprises $H_2$ generated via a water electrolysis unit comprising a water-electrolysis electrochemical cell, wherein the conduit conveying the $H_2$ for injection to the reactor vessel is coupled to the water electrolysis unit to receive $H_2$ as generated by the water electrolysis unit.

12. The method of claim 10, comprising providing at least one of the hydrogen, the carbon monoxide, or the carbon dioxide removed from the effluent to the olefin synthesis section, wherein the reactor vessel comprises internal metal divider plates for division into the dry reforming section, the heat exchange section, and the methanol synthesis section.

* * * * *